(12) United States Patent
Steckner et al.

(10) Patent No.: US 12,102,831 B2
(45) Date of Patent: Oct. 1, 2024

(54) CLINICAL STATIC STRIP MAGNET OF ALTERNATING POLARITIES TO PREVENT INADVERTENT ACTUATION OF MAGNET-MODE IN AN ACTIVE IMPLANTABLE MEDICAL DEVICE

(71) Applicant: Greatbatch Ltd., Clarence, NY (US)

(72) Inventors: Michael C. Steckner, Beachwood, OH (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 69 days.

(21) Appl. No.: 18/102,419

(22) Filed: Jan. 27, 2023

(65) Prior Publication Data
US 2023/0166115 A1    Jun. 1, 2023

Related U.S. Application Data

(63) Continuation of application No. 17/716,608, filed on Apr. 8, 2022, now Pat. No. 11,571,580.

(60) Provisional application No. 63/215,429, filed on Jun. 26, 2021, provisional application No. 63/174,498, filed on Apr. 13, 2021.

(51) Int. Cl.
*A61N 1/372* (2006.01)
*A61N 1/37* (2006.01)
*A61N 1/375* (2006.01)

(52) U.S. Cl.
CPC ....... *A61N 1/3718* (2013.01); *A61N 1/37512* (2017.08)

(58) Field of Classification Search
CPC .. A61N 1/08; A61N 1/36128; A61N 1/36142; A61N 1/37; A61N 1/3718; A61N 1/37211; A61N 1/37217; A61N 1/37223; A61N 1/37252; A61N 1/37254; A61N 1/3925
See application file for complete search history.

(56) References Cited

U.S. PATENT DOCUMENTS

| | | | |
|---|---|---|---|
| 3,391,697 | A | 7/1968 | Greatbatch |
| 3,774,619 | A | 11/1973 | Goldberg |

(Continued)

OTHER PUBLICATIONS

"ISO Standard 14117, "Active implantable medical devices—Electromagnetic compatibility—EMC test protocols for implantable cardiac pacemakers, implantable cardioverter defibrillators and cardiac resynchronization devices" (2019(".

(Continued)

*Primary Examiner* — Eugene T Wu
(74) *Attorney, Agent, or Firm* — Michael F. Scalise

(57) ABSTRACT

The present invention changes the magnet-mode of an active implantable medical device (AIMD) using a static strip magnet comprising at least a first, second and third magnet. The electronic circuits of the AIMD have been programmed to register when the static strip magnet has been swiped across the AIMD so that when the magnetic field-detection sensor detects a defined north and south polarity sequence of the first, second and third magnets, the electronic circuits have been programmed to enter into magnet-mode with electrical stimulation therapy of the body tissue and/or electrical sensing of biological signals from the body tissue being suspended, maintained in a preset mode, or placed in a programmed mode.

20 Claims, 33 Drawing Sheets

(56) References Cited

U.S. PATENT DOCUMENTS

| | | |
|---|---|---|
| 8,600,505 B2 | 12/2013 | Libbus et al. |
| 8,792,987 B2 | 7/2014 | Stevenson et al. |
| 10,561,837 B2 | 2/2020 | Stevenson et al. |
| 2003/0167078 A1* | 9/2003 | Weisner ............ A61N 1/37264 607/60 |
| 2006/0190060 A1 | 8/2006 | Greeninger et al. |
| 2012/0283588 A1 | 11/2012 | Lowy et al. |
| 2013/0158622 A1* | 6/2013 | Libbus ............... A61N 1/37217 607/30 |

OTHER PUBLICATIONS

Asher, Do, et al., "Smart Wearable Device Accessories May Interfere with Implantable Cardiac Devices", Asher Eb, Panda N, Trend Ct, Wu M, Smart Wearable Device Accessories May Interfere with Implantable Cardiac Devices, Heart Rhythm Case Reports (2021).

Greenberg M.D., et al., "Life Saving Therapy Inhibitions by iPhones Containing Magnets", Greenberg JC, Altawil MR, Singh G, Life Saving Therapy Inhibition by Phones Containing Magnets, Heart Rhythm (2021).

Shea, et al., "Unintentional Magnet Reversion of an Implanted Cardiac Defibrillator by an Electronic Cigarette".

Swerdlow, MD, FHRS, "CIEDs and Static Magnetic Fields 2021".

\* cited by examiner

Devices and Magnets

- Placing a strong magnet directly over a conventional pacemaker will switch its mode to asycnhonous:
  - AAI → AOO
  - VVI → VOO
  - DDD → DOO

- Indication:
  - Temporary use during electocautery
  - Termination or pacemaker-mediated tachycardia

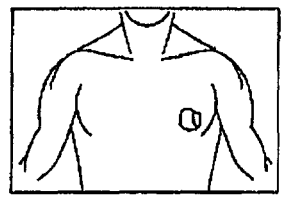

- *Usually*, a magnet will convert a pacemaker to asynchronous mode
  - Device response to magnet can be programmed
  - Rate depends on the manufacturing and the battery life
  - Asynchronous pacing mode depends on prior settings
    DDD → DOO    VVI → VOO    AAI → AOO
- Caution: Asynchronous rate may not always meet the physiological demands of the patient.
- Upon removal, device should revert to originally programmed pacing mode.

FIG. 1N

ICD:Magnet Summary

| Manufacturer | Response to Magnet | Effect on Pacer component of ICD | Tone Emmited? | Can ICD be programmed to ignore magnet? | Miscellaneous |
|---|---|---|---|---|---|
| Boston Scientific | ICD inhibited until magnet removed | None | Yes, beeping tone synchronoud with R-wave or every sec | Yes (Very rare) | Older ICDs that could be permannently deactivated with a magnet are gone Sub Q ICD respomds to a magnet. |
| Medtronic | ICD inhibited until magnet removed | None | Yes, monotone for 10-15 seconds only. High-low tone indicates device malfunction | Yes (Very rare) | Patient alerts can be programmed to emit an on-off tone with magnet application |
| St Jude | ICD inhibited until magnet removed | None | No | Yes (Very rare) | |
| Biotronik | ICD inhibited until magnet removed | None | No | No | Magnet will inhibit ICD for 8 hours only. Would have to remove and replace ICD to extend inhibition |
| Sorin | ICD inhibited until magnet removed | Converts pacer rate to 96->80 depending on battery life. Pacing mode unchanged | No | No | No option to convert to an asychronous pacing mode even when the ICD is inhibited with a programer |

FIG. 10

CLINICAL STATIC STRIP MAGNET OF ALTERNATING POLARITIES TO PREVENT INADVERTENT ACTUATION OF MAGNET-MODE IN AN ACTIVE IMPLANTABLE MEDICAL DEVICE

CROSS-REFERENCE TO RELATED APPLICATIONS

This application is a continuation of U.S. application Ser. No. 17/716,608, filed on Apr. 8, 2022, now U.S. Pat. No. 11,571,580, which claims priority to U.S. provisional application Ser. No. 63/174,498, filed on Apr. 13, 2021, and 63/215,429, filed on Jun. 26, 2021.

BACKGROUND OF THE INVENTION

1. Field of the Invention

The present invention generally relates to active implantable medical devices (AIMDs), including cardiac pacemakers, implantable cardioverter defibrillators (ICD), deep brain stimulators, spinal cord stimulators, and the like. The present invention is particularly important for patients who have an AIMD with a magnet-mode. Placement of a permanent (i.e., time-constant) magnet over an AIMD has been used for many decades as a simple way to place the device into magnet-mode to either suspend therapy or enter a preset therapy mode. In fact, even before the introduction of telemetric communication with pacemakers in the 1970s, magnets were used to alter pacing behavior in order to demonstrate functionality such as remaining battery life or to achieve asynchronous pacing when electromagnetic interference (EMI) was suspected.

2. Prior Art

U.S. patent application Ser. No. 05/216,667 was filed on Jan. 10, 1972 and is one of the earliest disclosures related to magnet-mode as a test for assessing battery life or a patient's heart rate. The '667 application subsequently issued as U.S. Pat. No. 3,774,619. The filing of the '667 application was just four years after the first implantable pacemaker patent (U.S. Pat. No. 3,391,697) issued on Jul. 9, 1968 to Wilson Greatbatch. Currently, most cardiac pacemakers and implantable defibrillators have a magnet-mode where a static magnet of a sufficient strength (the clinical magnet) is placed over the AIMD implant. The AIMD senses the static magnetic field and then switches into its predetermined "magnet mode." In general, a clinical magnet used for this purpose is on the order of 70 to 120 Gauss.

Many deep brain stimulators and spinal cord stimulators also have a magnet-mode. Consequently, implantable medical devices, particularly cardiac implantable medical devices (CIED), are by design susceptible to external magnetic fields. Particular to this invention, external magnetic fields are called static magnetic fields because they provide a constant magnetic field over time.

There has been a proliferation of relatively strong magnets being placed in portable electronic devices, toys, and the like. As will be explained, there have been recent case reports of magnets built into a cell phone causing implantable cardioverter defibrillators (ICD) and pacemakers to enter magnet-mode. In the case of an ICD, this is alarming because magnet-mode suspends tachyarrhythmia detection and, therefore, suspends high-voltage therapy. Bearing in mind the gravity of suspended tachyarrhythmia detection, that being suspension of life-saving therapy delivery, placing a magnet into a portable device, instrument, toy, and the like, becomes a considerable concern as when a human impulsively places a strong magnet, such as contained in an iPhone 12, in a shirt, jacket or vest pocket, a bra, a fanny pack, a drug pump, or other similarly worn accessories or clothing. Many toddlers and even infants receive AIMD implants so the cohort of patients that play with toys is significant. IPHONE® is a registered trademark of Apple Inc., Cupertino, CA.

Such an impulsive action can inadvertently position the strong magnet housed inside the device unfavorably over an AIMD implant. Cardiac implants including pacemakers and ICDs are typically implanted in a pectoral pocket. Spinal cord stimulators are often implanted in the groin or buttocks. Deep brain stimulators may also be pectorally implanted or they may be cranial implants or even both. The presence of a strong magnet in close proximity to these types of implanted medical devices can cause dangerous and inadvertent activation of the device's magnet-mode.

In that respect, inappropriate (even improper) interaction of the iPhone 12 with an ICD has been the subject of recent worldwide news. Correspondingly, patient anxiety issues regarding cell phone safety have also emerged. Medical doctors and pacemaker committee members, including co-inventor Robert Stevenson, have received numerous calls from anxious patients. For example, a call recently received by Robert Stevenson concerned a grandfather worried about his grandchild's iPhone 12S entering his house. In the first place, a patient with tachyarrhythmias generally experiences anxiety just knowing that they need to have an AIMD implant that shocks their heart when it chaotically beats. Worrying about the safety of the implant can cause increased stress for a patient that could possibly lead to other stress-induced health issues. An important effect of the present invention on a patient's mental well-being is that the present invention ensures the patient that inadvertent magnet-mode entry of their implanted AIMD is mitigated (rendered highly unlikely) and even prevented by applying the deliberate and unique (novel) actions taught herein.

Even though both ICDs and pacemakers, by design, have a magnet-mode response, not all manufacturers' magnet-mode responses are identical. In general, however, for all ICDs, high-voltage therapy is suspended during placement of a magnet over the device, and for a cardiac pacemaker, the IPG is put into what's commonly known as a fixed rate or asynchronous pacing mode. During asynchronous pacing mode, if a bradycardia patient is not in bradycardia (in other words, has a normal heartbeat), a rate competition can occur. This means that the patient's underlying sinus rhythm is not in synchrony with the magnet-mode asynchronous beats of the cardiac pacemaker. Prolonged asynchronous pacing (for example, if a patient were to fall asleep with the magnet of their cell phone positioned over their pocket all night) is not desirable. For some patients, rate competition can result in reduced cardiac output also known as reduced hemodynamic output, which can make the patient feel ill including loss of energy. Also, prolonged asynchronous pacing is undesirable because it can lead to heart tissue remodeling. Additionally, a rare "pace on T" event (also known as a "r on T" event) can occur if the asynchronous pacemaker pulse repeatedly lands on the part of the cardiac rhythm cycle known as the T wave. In this case, ventricular fibrillation (VF) can be induced, which is immediately life-threatening. Again, this is a very rare event.

There are also magnet-mode responses designed into other types of implantable medical devices, for example, deep brain and spinal cord stimulators. Testing the immunity of a cardiac implantable medical device (CIED) to an electromagnetic field or electromagnetic interference (EMI) is defined by international ISO standard 14117. The ISO standard was originally known as AAMI PC69, of which coinventor Robert A. Stevenson was one of the original committee members (PC69 became worldwide ISO Standard 14117 titled "Active implantable medical devices—Electromagnetic compatibility—EMC test protocols for implantable cardiac pacemakers, implantable cardioverter defibrillators and cardiac resynchronization devices").

Robert A. Stevenson is also a United States Technical Representative to ISO and part of the ISO 14117 Committee. For many years, Robert A. Stevenson has been the co-chairman of the United States Pacemaker Committee (Association for the Advancement of Medical Instrumentation-Cardiac Rhythm Management Device Committee (AAMI-CRMD), additionally referred to as CRMD.

Since January 2021 after the first Heart Rhythm Society case report emerged about an iPhone 12 causing an ICD to inadvertently enter magnet-mode, there has been a series of Pacemaker Committee teleconferences. These meetings have been in conjunction with many doctors, implantable device manufacturers and the FDA Office of Science and Engineering Labs. Testing by the FDA has confirmed that the static magnetic fields emanating from an iPhone® 12 greatly exceed the 10 Gauss (1 mT) limit required for an implantable device to enter magnet-mode at the approximate depth which an ICD or an IPG is typically implanted in a patient, as specified in ISO 14117. The FDA has confirmed that the static magnetic fields emanating from the top of an iPhone 12 are greater than 300 Gauss (30 mT), which far exceeds the ISO 14117 10 Gauss limit. The FDA has also confirmed that strong magnetic fields in excess of 700 Gauss (70 mT) are produced by the Apple watch.

Table 1 below summarizes the static magnetic field mapping data presented by the FDA to the Pacemaker Committee on Mar. 3, 2021 (all data in Gauss).

TABLE 1

| | EUT model | | | | |
|---|---|---|---|---|---|
| Distance | iPhone 12 Pro Max | iPhone 12 Pro | iPhone 12 | iPhone 12 Mini | Apple Watch |
| 1 mm** | 363 | — | — | — | — |
| 1 mm* | 114 | 84 | 90.7 | 59.9 | 778 |
| 11 mm* | 15.2 | 16.7 | 16 | 13.1 | 34.5 |
| 21 mm* | 7.9 | 8.5 | 8.1 | 6.5 | 6.7 |
| 31 mm* | 3.6 | 3.7 | 3.7 | 3.1 | 1.8 |

*Measured from the top of camera or from the top of the watch
**Measured from the top of phone main body It was in this context that co-inventors Michael Steckner and Robert Stevenson collaborated on how to prevent inadvertent entry of an AIMD into magnet-mode.

At the outset, it should be mentioned that there are other approaches for a safer alternative to magnet-mode that the inventors studied and discarded. The first approach was to simply eliminate AIMD magnet-mode. However, many of the physicians who participated in these teleconferences have pointed out that a simple way to enter magnet-mode was essential. Some of the reasons why an emergency responder, doctor, surgeon or even the patient may place a magnet over an AIMD include:

1) Sometimes an ICD has a lead failure or other issue, which can cause the device to repeatedly deliver painful and inappropriate high-voltage shocks. In this situation, a magnet is quickly placed over the ICD to suspend such painful shocks while the patient is transported to an appropriate hospital, and the like.

2) In a pacemaker patient, and this depends on individual programming, positioning a magnet over the medical device places the pacemaker in an asynchronous pacing mode that could be at a higher pacing capture threshold than the patient needs. In other words, for a patient in cardiac distress, placing a magnet over the medical device can immediately cause the pacemaker to pace at a higher level than what they need, again, during the time that the patient is being transported or evaluated.

3) During surgery it is common practice to place a magnet over the patient's implanted device, for example, to suspend deep brain stimulation, suspend spinal cord stimulation or for an ICD to suspend high-voltage shock therapy. ICD therapy is frequently suspended, for example, during a delicate surgery like a robotic-assisted pancreas resection. The reason is that should an automatic high voltage shock from an AIMD occur, the shock could cause the sedated patient's body to suddenly and violently jump (surgeons call this "jumping off the table"). For example, one thing that could cause an ICD to deliver an automated high voltage shock during surgery is electromagnetic interference noise produced by electrocautery. However, temporarily placing an AIMD in magnet-mode during surgery is not a concern because the patient's EKG waveforms are being continuously monitored by the anesthesiologist during surgery. Should the patient need to be defibrillated during surgery, therapy can be performed by an external cardiac defibrillator.

Several Pacemaker Committee doctors have also pointed out that the clinical donut-shaped magnets that are used to deliberately place an AIMD into magnet-mode are present world-world from little clinics to emergency rooms to hospitals to ambulances, and the like. Consequently, magnet-mode represents a universal long-standing and highly regarded protocol for rapid intervention. The present inventors also studied existing BLUETOOTH-enabled devices that can communicate with an AIMD. (BLUETOOTH is a registered trademark of Bluetooth Sig, Inc., Kirkland, Washington)

Cell phone apps were also examined. The problem with a cell phone app is how rapidly a secure connection can be established with an ICD and the ability of an ICD-dependent patient to self-administer when painful high voltage shocks are being discharged into their body. Moreover, there is an inherent cyber security benefit in having to place a clinical donut-shaped magnet directly over the patient's implant. The static clinical magnets that are used to induce magnet-mode are about 70 to 120 Gauss and only work in close proximity to the implanted AIMD (closer than about 15 cm or six inches). The longstanding practice of placing a static magnet over the patient's AIMD is inherently cyber security secure because the magnet must be in very close proximity to the patient's skin or clothing, which is an invasion of the patient's space that the patient would generally be aware of. In addition, many remote areas and clinics around the world do not have cellular phone coverage and some clinicians do not even own a cell phone.

One of the concerns with any wireless or BLUETOOTH® attempt at communication with an AIMD is that such communication could induce magnet-mode over a greater distance which could open up the threat for hackers, and the like. ISO 14117 has a clause that specifies that no CIED (pacemaker or ICD) can enter magnet-mode at a static magnetic field strength below 1 millitesla (10 Gauss). However, this is as much a human factor situation as it is one of technical specifications. International Standards and National Standards that limit the fields from an emitter are not always in harmony with ISO 14117.

Human factors are a great concern when analyzing any AIMD/CIED potential static magnetic field interaction. For example, stereo speakers, such as tower speakers used in a home theater system, have very powerful magnets. If an AIMD-dependent patient removed one of these speakers from its cabinet and then flipped the speaker over so that the strong magnet is placed directly over their implant, this could cause their implanted device to enter magnet-mode. While such a scenario is highly unlikely, one could even argue that instead of inadvertent entry into magnet-mode, it was deliberate.

A recent case reported in a Heart Rhythm Society (HRS) prepublication titled: Life Saving Therapy Inhibition by iPhones Containing Magnets, Greenberg, M.D. et al., describes that when an iPhone 12 was placed over a patient's pectoral area, the phone's magnet undesirably induced an ICD magnet-mode. This was validated and verified by the FDA Office of Science and Engineering Laboratories (FDA-OSEL). In comparison to previous iPhone® models, the iPhone 12 and the newer iPhone 13 have a system called MAGSAFE®, which means that a powerful permanent ring magnet that produces a static magnetic field resides inside the phone to assist in alignment of the phone with an external wireless charging docking pad, wireless charging wand, and the like. MAGSAFE is primarily designed to work with a coiled wire in the external charging device that transmits a time varying magnetic field intended to couple its energy in a transformer-like action to a charging coil embedded in the iPhone 12. An Apple watch can be charged in a similar manner.

The CRMD has a formal relationship with the FDA, the Heart Rhythm Society and its doctors and clinicians. In particular, members of the HRS Health Policy Committee and Interoperability Workgroup are members of the Cardiac Rhythm Management Device (CRMD) Committee and vice versa. The CRMD has been made aware that Samsung and other Android cell phone manufacturers may also be incorporating permanent magnets into their device. This has not yet been validated. However, Greatbatch Ltd., Clarence, New York, has obtained high-resolution CT images of an iPhone 12, an iPhone 13 and an Apple watch. These images, which were provided to the CRMD Committee and are included herein (see FIGS. 8A, 8B and 8C), show a large permanent charging alignment ring magnet 232 housed inside the device. It should be pointed out that neither Apple nor any other manufacturer of portable electronic devices containing a magnet has violated any standard or any regulation. This is simply an unregulated space. Again, inadvertently placing a cardiac implantable medical device (CIED) or AIMD in magnet-mode is as much a human-factor concern as anything.

A first step in working with the FDA Office of Science and Engineering Labs (OSEL) was to precisely map the static magnetic fields of an iPhone® 12 and Apple watch at various distances and spatial orientations (Reference: Table 1 above). CRMD and the present inventors then compared the static magnetic fields produced by the iPhone® to ISO 14117 to assess the potential for interference with an ICD or pacemaker or other type of AIMD. The static magnetic field maps of the iPhone 12 were found to greatly exceed the ISO 14117 magnet-mode threshold.

There have also been a number of reports of the relatively weaker magnets in earbuds or the relatively small and weaker magnet in an iPad or a Kindle cover inducing a magnet-mode response in an AIMD. The CRMD has been watching these papers for years and has conducted numerous interviews with the authors to assess the human factors. In each case, the author reported it was difficult to find the "sweet spot" that induced magnet-mode and it was particularly difficult to hold onto magnet-mode, particularly with any movement of the patient. The CRMD Committee has looked at these situations and concluded that it would be highly unlikely for an iPad or a Kindle cover type of device containing a magnet to induce a prolonged (not transient) and, therefore, dangerous magnet-mode response.

However, a recent case report involving an iPhone 12 is of concern from a human-factor point of view. It is common surgical practice to position a cardiac implantable medical device (CIED) or AIMD in a pectoral pocket. The CIED is then connected to one or more leads that are routed transvenously to distal electrodes in contact with cardiac tissue. As previously described, when a relatively strong magnet (clinical magnet) is placed directly over the CIED, the device's magnet sensors are designed to put the device into magnet-mode. Older style (legacy) CIEDs have reed switch sensors that switch in the presence of a strong magnetic field (a reed switch is unable to detect north-south polarity but can detect the minimum amplitude of the static magnetic field). Most present-day implantable devices use a Hall-effect sensor which is designed to detect a static magnetic field of specified amplitude (Hall-effect sensors can be programmed to detect north-south or south-north magnetic field polarity, however, no AIMD is presently designed or programmed to do so). A giant magnetorestive (GMR) sensor, which is rarely used in current AIMD designs, cannot be programmed to detect north-south clinical magnet reversals. This is yet another reason for the alternative to count multiple placements within specified constraints (ref. FIG. 9). This enables AIMDs with Hall-effect and GMR based sensors, and the like, to be more resistant to inadvertent entry into magnet-mode.

As used herein, "n" comes from mathematics, meaning "n" can be any number. The letter "n" can be the number of placements, "n" can be the number of flips, or "n" can denote an application time in seconds or removal time in seconds. The letter "n" with subscripts, for example, can be used to specify a minimum and a maximum placement or clinical magnet removal time. In summary, and as defined herein, the use of the letter "n" has to be taken in context as it can have multiple meanings.

Thus, a feature of the present invention is to: 1) detect and count multiple placements of the magnet over the AIMD or, 2) sense the polarity (north-south) flips of the static magnetic field emanating from a clinical magnet (the N-S flip counting is a preferred embodiment as this is the most resistant to inadvertent magnet-mode entry). Ideally, these two approaches are integrated into one methodology. This would require reprogramming the AIMD to either sense the number of placements within a specific time period ("n"-placements) or, to detect the number of polarity flips within a specific time frame. Older legacy style AIMDs or even newer AIMDs with reed switches cannot be programmed to detect north or south polarity from a clinical magnet. However, in contrast with a mechanical reed switch and in accordance with the present invention, most AIMDs now have an electronic Hall-effect sensor that can be programmed or even re-designed to detect north-south polarity reversals (or flips) from a clinical magnet. That is even though no AIMD in use today is programmed to do so.

In a preferred embodiment of the present invention, a new clinical method is described wherein: a clinical magnet (without the clinician or patient placing the magnet needing to know which side is north or south) is simply placed over the AIMD for a time (for example, count to three in one's head), then the magnet is removed again (count again), flipped over (count again), and then the magnet is repositioned over the AIMD. This sequence can be repeated for any number of times "n". In this case, when "n" is defined as the total number of flips, and when n=3, the procedure is referred to as the "Triple Flip", (international cardiac societies are contemplating the number of flips and placements of the clinical magnet over the AIMD implant). In this way, all clinical magnets would be repetitively placed, timed and flipped. It is not important that the clinician understand whether the AIMD is sensing the number of placements and time periods or that the AIMD is also sensing the placements and the number of north-south polarity reversals (flips) as the clinical methodology is the same for both situations. Note that "n" flips require n+1 placements.

It would be highly unlikely to remove an iPhone 12 or an iPhone 13 from a shirt pocket for a few seconds and then place it back in the pocket, then remove it from the pocket for a similar number of seconds and then place it back in the pocket ("n"-number of times). It is even more unlikely that the cell phone would be flipped each time, which would require n+1 placements, each time doing a north-south polarity reversal. Further, the measured static magnetic fields emanating from the back of an iPhone are much higher than at the front face of the phone, so it is further unlikely that an iPhone could inadvertently induce north-south or south-north flips (this depends upon implant depth below the skin, patient body-mass-index (BMI) and other factors).

In that respect, it is a goal of the present invention that the multiple placements or polarity flips of a clinical magnet over an AIMD be compatible with almost all AIMD design platforms in the world. Again, as stated, this is going to require AIMD reprogramming (or is some cases re-design) in order to detect the number of magnet placements and their timing or the number of magnet flips, or both, before the device enters into magnet-mode. It is contemplated that the clinician would use a surgical skin marker, a piece of tape (a tape dot) or equivalent to place a dot on the patient's skin or clothing over the implant so that the clinical magnet is repositioned over the AIMD in the same manner after each placement or flip.

ISO 14117 does not specify the static magnetic field strength at which an implantable device must enter magnet-mode. Instead, ISO 14117 specifies the magnetic field floor below which the device must not enter magnet-mode. The ISO 14117 magnetic field floor is specified as 1 millitesla (i.e., a 10 Gauss limit). As will be described hereinafter in the detailed description of the invention, the present inventors believe that, from a human-factors point of view, building any portable electronic device that can be placed in a shirt pocket or over an implant for an extended period of time, is potentially dangerous in that the AIMD may inadvertently (inappropriately) enter into magnet-mode. NOTE: this ISO 14117 10 Gauss level has a +/−1 Gauss tolerance, which means that an AIMD can enter magnet-mode at 9 Gauss (0.9 mT). Hence, as the growing popularity of consumer products with powerful magnets is likely to become even more common in the future, it is incumbent that the magnet-mode response of an AIMD be changed in order to avoid a growing and potentially life-threatening patient safety concern.

Reference is now made to a paper presented at the Heart Rhythm Society Annual Scientific Sessions on Jul. 29, 2021 by Dr. Charles Swerdlow, MD, Fellow of HRS and a member of the faculty at Cedars Sinai Medical Center. The title of the paper is "CIEDs and Static Magnetic Fields 2021." During preparation of the paper (assisted by Robert Stevenson), several interesting new static field emitters were documented. They are summarized as follows: 1) wristbands for watches that have a magnetic clasp significantly exceed 10 Gauss, 2) a wrist worn magnetic tool belt that holds devices like an Allen wrench, and the like, has a very powerful magnet, 3) magnetic implants to hold jewelry in place, 4) magnetic badge buttons, and 5) a Nikken 1 Power chip Medallion Charm manufactured by Kenco, which is attached to a lanyard worn around the neck or placed over any body area. The Nikken 1 advertises a magnetic field strength of 900-1000 Gauss. This is very worrisome as 10-Gauss is the ISO 14117 limit for CIED magnet mode. One of the CRMD members has pointed out that children's toys are also starting to show up with strong magnets, such as a large teddy bear that has a magnet that allows it to be stuck on the refrigerator. It seems that with the reduced cost and availability of neodymium there is a proliferation of devices with strong magnets.

There are also two other case reports of interest. The first is titled, Smart Wearable Device Accessories May Interfere with Implantable Cardiac Devices. The citation for this article is: Asher Eb, Panda N, Trend Ct, Wu M, Smart Wearable Device Accessories May Interfere with Implantable Cardiac Devices, Heart Rhythm Case Reports (2021). The key takeaway from this article is that magnets used in the wristbands of fitness trackers and Smart watches, and the like, can interfere with implanted cardiac devices through inducing an inappropriate magnet-mode response.

Another Heart Rhythm Society case report which comes from the Cardiovascular Arrhythmia Service, Brigham and Women's Hospital and Harvard Medical School is titled, Unintentional Magnet Reversion of An Implanted Cardiac Defibrillator by An Electronic Cigarette, authored by Tedrow, M. D. et al.

The present inventors are also aware of a recent case report out of Calgary, Canada involving a patient with a spinal cord stimulator (SCS). The SCS was designed with a magnet-mode, which means that when a clinical magnet is applied to the device, therapy is suspended so that the patient can control the device using an external handheld programmer. The handheld programmer can turn the SCS on and off, select what electrodes the patient wants to use to deliver pain relief therapy, adjust the amplitude of the waveforms, all while therapeutic electrical pulses are being sent to the spine. In this patient, the SCS was implanted low in the patient's groin on the right side. Consequently, when the patient placed an iPhone 12 in the front pocket of his pants, the first indication that something was wrong was when the patient suddenly experienced severe lumbar spinal cord pain. The patient did not understand what was happening and in pain, started to twist and contort in an attempt to get himself into a more comfortable position. It is known that twisting and contorting can cause the electrode bundle that is in the spinal cord canal to shift, which can change the efficacy of the therapy being delivered. Spinal cord stimulator patients are generally provided with an external control device (a patient handheld programmer) so that they can regulate the active electrode pairs, stimulation therapy and even the waveforms that mitigate pain. Pain mitigation is known as maximum paresthesia (paresthesia that overrides the pain sensations and stops them from transiting to the spinal cord nerve).

By shifting and contorting in an attempt to relieve pain, the Calgary patient's iPhone 12 was inadvertently being intermittently positioned over the SCS implant. By design, re-application of a magnet turns the SCS back on so that therapy is once again delivered. It is likely that the electrode bundles in the patient's spinal column had shifted sufficiently such that, when the SCS was turned back on, the delivered therapy caused the patient to experience a jolting, stabbing pain that sent the patient to the floor. The patient described the experience as similar to being tasered or receiving a powerful electrical shock. Amazingly, the patent at a later time, laid on his back without moving (in other words, so the electrode bundles didn't shift) and discovered that he could repeatedly turn on and off his SCS therapy with the iPhone 12. The Calgary patient further reported that his situation could have been markedly worse had he been driving when the initial jolting shock occurred.

It is also noted that a deep brain stimulator (DBS) has a similar magnet-mode where proper placement of a clinical magnet is designed to suspend therapy. Suspension of therapy in a patient with severe Parkinson's or Tourette's Syndrome, for example, can lead to uncontrolled and sometimes violent patient motions, which cannot be controlled without a DBS. A human-factor concern regarding DBS devices is that if therapy is inadvertently suspended, for example, while the patient is operating a motor vehicle, uncontrolled tremors could result in an automobile accident.

It is also noted that a deep brain stimulator senses electrical brain wave activity to provide therapy to prevent an epileptic seizure from occurring. Candidates for a deep brain stimulator implant typically experience fairly frequent epileptic seizure episodes. It is the general practice that such patients are not able to have a driver's license. However, after implantation of a DBS device to prevent epileptic seizures, these patients can return to normal daily life activities, including driving. This presents another potential human-factor issue where inadvertent placement of a magnet over the DBS could suspend device therapy. If suspension of device therapy were to happen coincident with the onset of a seizure, this could of course, be very dangerous, for example, when the patient is driving a motor vehicle.

Refer now to U.S. Pat. No. 8,600,505, which relates to an externally-controlled Vagus nerve stimulator (VNS) for "treating chronic cardiac dysfunction". Beginning on column 15, line 51, this patent describes that "[o]rdinarily, the surface 101 of the patient magnet must be applied to or swiped, that is, moved in a continuous motion, over the neurostimulator 12 for at least one second to protect against the reed switch 30 being inadvertently triggered by other magnetic sources." Then, beginning at column 16, line 17, the '505 patent states that, "[t]he instructions 104 can walk the patient 10 through the individual physical steps necessary to properly use a magnet, including what swipe pattern to use and providing a countdown of how long to hold the magnet over the neurostimulator 12." At column 16, lines 28, the '505 patent states that, "[t]ypically, a neurostimulator 12 will inhibit stimulation indefinitely for as long as a patient magnet 100 remains in place. If a patient 10 suffers a crisis, such as significant pain or discomfort, VNS can be stopped for an indefinite amount of time by fixing the patient magnet 100 in place over the neurostimulator 12, such as by taping the magnet to the chest, until professional help can be sought." When one considers the large and powerful ring magnet in the back of an iPhone 12 and imagines, for example, placing the iPhone 12 in the upper pocket of a fly-fishing vest, one can see the potential for repeated and inadvertent swipe patterns. The cell phone pocket for a fly-fishing vest is placed high in the pectoral area directly over where an AIMD would typically be implanted. A fly-fisherman is constantly contorting his chest and could be moving or swiping the iPhone 12 almost continually over the implant. It is hard to imagine how many inadvertent applications of magnet-mode or different therapy levels might be induced.

Referring back to the '505 patent, the disclosure beginning on column 17, line 10 describes "through magnet-mode, such as one swipe signaling a one-hour suspension, two swipes signaling a four-hour suspension, and three swipes signaling an eight-hour suspension for when the patient goes to bed and wants to suspend stimulation while he is asleep." The '505 patent goes on to state, "[o]ther manner of accommodating multiple stimulation modes are inefficient for the use of a patient magnet 100 are possible." Again, given the proliferation of powerful magnets, such as in the iPhone 12, one can see that the '505 patent is another example of a very dangerous situation where inadvertent entry into magnet-mode could suspend important therapy for long periods of time.

SUMMARY OF THE INVENTION

The present invention resolves the concerns discussed above regarding inadvertent or inappropriate entry into magnet-mode for an AIMD when exposed to an electronic device, such as an iPhone 12 or iPhone 13, a child's toy with a strong magnet, and the like. The invention disclosed herein applies to AIMDs with both older generation reed switches, GMR sensors and newer generation AIMDs that generally have an internal Hall-effect sensor, also known as a magnetic field sensor. More particularly, in one embodiment, the present invention teaches reprogramming an AIMD with a magnet-mode that can detect a number of placements of a clinical magnet over the implanted AIMD within a specified time period and for a specified duration and only then does the AIMD enter into magnet-mode. In another embodiment, the present invention teaches deliberately flipping a clinical magnet (e.g., magnet polarity inversion) over an AIMD multiple times in a particular time sequence, which significantly reduces the likelihood of inadvertent magnet-mode and effectively mitigates and prevents an AIMD from being inadvertently triggered (switched) into magnet-mode.

In one embodiment, flipping the magnet is known as "The Double-Flip". The Double-Flip is attained when a clinician first places a magnet over the AIMD, then flips the magnet over and places the opposite polarity of the magnet against the AIMD, followed by a second flip with placement of the magnet back to its original polarity over the AIMD. Polarity sensitivity is realized with Hall-effect or alternative similar sensors internal to the AIMD, where the novel circuitry described by the present invention is programmed to enter magnet-mode on detecting a defined flip and time sequence. Three clinical magnet flips relate to the title of the invention, which embodies the "The Triple Flip", which requires four placements of the clinical magnet within a specified time sequence.

In summary, the present invention relates to reprogramming an AIMD with a magnet-mode so that either multiple placements of a clinical magnet over the device within a specified time period are sensed or multiple placements of a clinical magnet over the device while each time flipping the magnet are sensed by the device. From the clinician's point of view when placing a clinical magnet over a device, the clinician does not need to know how the AIMD is designed or re-programmed to sense the static field from the magnet or the magnet's polarity. All the clinician has to do, for example, for "The Triple Flip" technique, is to place the clinical magnet over the AIMD within a specified period of time (four times), each time turning the magnet over so that there is a north-south reversal. The AIMD is programmed to count this as a specified number of magnet placements, or if the device has the capability of detecting north or south polarity, the AIMD will also record the number of flips. In either case, the result is that the AIMD will enter magnet-mode after the proper number of placements of the clinical magnet over the AIMD or the proper number of placements of the clinical magnet over the AIMD along with the proper number of flips.

The present invention also teaches another feature that often arises when an AIMD patient, such as a CIED patient, is being transported in a medical emergency, for example, in an ambulance. While rare, from time-to-time an ICD patient can have a defective lead that becomes "noisy", thereby causing the ICD to falsely detect and continuously deliver painful and inappropriate high-voltage shocks. In this case, the clinical magnet is first placed over the ICD to suspend high-voltage therapy and then the magnet is taped in place until the patient reaches a hospital, a pacemaker center or a clinic where the device or leads can be replaced (or at least re-set). The present invention includes a feature within the AIMD programming where once the proper number of placements or flips have been detected and the device enters magnet-mode, the AIMD stays in magnet-mode for a programed period of time or for as long as either the north or the south face of the clinical magnet is in place over the device (taped in place). As such, the primary purpose of the present invention is to prevent an AIMD from inadvertently entering magnet-mode. A secondary purpose of the present invention is to preserve the usefulness of the millions of clinical magnets that are in doctor's offices, hospitals, emergency rooms, stuck on file cabinets, in ambulances, and even in remote areas of the world without electricity. Preventing an AIMD from being inadvertently triggered into magnet-mode is crucial to patient safety, particularly in light of the proliferation of permanent magnets, not only in the iPhone 12 and the iPhone 13 and their ring magnet designs, but also in smart watches including the APPLE® watch, magnet wrist bands, KINDLE® covers (KINDLE is a registered trademark of Amazon Technologies, Inc., Seattle Washington), iPAD® covers (iPAD is a registered trademark of Apple Inc., Cupertino, CA), FITBITS®, (FITBIT is a registered trademark of Fitbit, Inc., San Francisco, CA) certain electronic cigarettes and even magnetic earbuds, and the like.

Further regarding the iPhone 12, when a cell phone is naturally and naively placed in a person's shirt pocket, coat pocket, vest pocket (e.g., a fly-fishing vest pocket), bra, under garment pocket, fanny pack or other similarly worn accessories or clothing, the magnet of the iPhone 12 can inappropriately suspend ICD high-voltage therapy (these are typically implanted in a pectoral pocket which could align with a shirt pocket, etc.). This could endanger the life of a patient should a dangerous tachyarrhythmia arise. Suspending life-saving high-voltage shock therapy for an extended period of time is potentially harmful and even life-threatening to the patient because, if the patient enters into a dangerous arrythmia, such as ventricular fibrillation (VF), the ICD would be disabled and unable to provide high-voltage, life-saving shock therapy to the patient's heart.

With a powerful magnet inappropriately held over the ICD, the ability to deliver a high-voltage shock to a chaotically beating heart is prevented. In other words, as long as the magnet is sensed by the ICD, it is not possible for the ICD to cardiovert the patient's chaotic heart rhythm into a life-sustaining heart rhythm. However, the double or multiple magnet applications or magnet flips of the present invention effectively prevents such life-threatening situations.

Additionally, a triple magnet application or triple magnet flip (or more, including n-flips) according to the present invention provides an even higher degree of patient safety. As disclosed herein, these magnet applications or magnet flips must be performed within a specific time sequence so that inadvertent entry into AIMD magnet-mode becomes even more unlikely.

Further, a recent sequence of CT scans taken by Greatbatch Ltd., Clarence, New York, of an iPhone 13 show that the phone has a similar or even larger toroidal magnet as previously described for an iPhone 12. In addition, Apple's worldwide warnings include advising patients to keep an iPhone 12 or an iPhone 13 at least 15 cm (6 inches) from an implanted AIMD. In other words, the present concern is certainly not limited to just the iPhone 12.

Thus, the present invention relates to an active implantable medical device (AIMD), comprising a housing for the AIMD, the housing containing a magnet-detection sensor connected to electronic circuits, wherein the electronic circuits have been programmed to register when the magnet-detection sensor detects that a magnet is in close proximity to the AIMD as a first proximity occurrence, and wherein, within a defined first-time window upon commencement of the first proximity occurrence, the electronic circuits have been programmed to register when the magnet-detection sensor no longer detects that the magnet is in close proximity to the AIMD as a first removal occurrence, and wherein, within a defined second-time window upon commencement of the first removal occurrence, the electronic circuits have been programmed to register when the magnet-detection sensor again detects that the magnet is in close proximity to the AIMD as a second proximity occurrence to thereby cause the electronic circuits of the AIMD to enter into magnet-mode. Further, upon commencement of the second proximity occurrence, the electronic circuits have been programmed to remain in magnet-mode for as long as the magnet-detection sensor detects that the magnet is in close proximity to the AIMD, wherein the magnetic-detection sensor is configured to detect the close proximity of the magnet having a strength of at least about 9 Gauss. The magnet-detection sensor is selected from the group of a reed switch, a Hall-effect sensor and a giant magnetoresistive (GMR) sensor. Further, the first-time window has a duration of from $n_1$ seconds to $n_2$ seconds, and the second-time window has a duration of from $n_3$ to $n_4$ seconds, wherein $n_1$ and $n_3$ seconds are the same or different and $n_2$ and $n_4$ seconds are the same or different or, the first-time window has a duration of from 2 to 10 seconds, and wherein the second-time window has a duration of from 2 to 10 seconds.

The present invention further relates to an AIMD wherein, instead of entering into magnet-mode upon commencement of the second proximity occurrence, the electronic circuits have been programmed not to enter into magnet-mode upon commencement of the second proximity occurrence, and wherein, within a defined third-time window upon commencement of the second proximity occurrence, the electronic circuits have been programmed to register when the magnetic-detection sensor no longer detects that the magnet is in close proximity to the AIMD as a second removal occurrence, and wherein, within a defined fourth-time window upon commencement of the second removal occurrence, the electronic circuits have been programmed to register when the magnetic-detection sensor again detects that the magnet is in close proximity to the AIMD as a third proximity occurrence to thereby cause the electronic circuits of the AIMD to enter into magnet-mode, and wherein, upon commencement of the third proximity occurrence, the electronic circuits have been programmed to remain in magnet-mode for as long as the magnetic-detection sensor detects that the magnet is in close proximity to the AIMD.

The present invention further relates to an AIMD wherein, instead of entering into magnet-mode upon commencement of the second proximity occurrence, the electronic circuits have been programmed not to enter into magnet-mode upon commencement of the second proximity occurrence, and wherein, within a defined second plus x-time window after commencement of the second proximity occurrence, the electronic circuits have been programmed to register when the magnetic-detection sensor detects that the magnet is no longer in close proximity to the AIMD as a first plus x additional removal occurrence, and wherein, within a defined second plus x+1-time window after commencement of the first plus x removal occurrence, the electronic circuits have been programmed to register when the magnetic-detection sensor again detects that the magnet is in close proximity to the AIMD as an additional proximity occurrence to thereby cause the electronic circuits of the AIMD to enter into magnet-mode, wherein x in the second plus x-time window is the same as in the first plus x additional removal occurrence and in the second plus x+1-time window, and wherein x=1 to 100, and wherein, upon the additional x+1 proximity occurrence, the electronic circuits have been programmed to remain in magnet-mode for as long as the magnetic-detection sensor detects that the magnet is in close proximity to the AIMD.

The present invention further relates to an AIMD that comprises a lead wire connected to the AIMD, wherein the lead wire extends to a distal electrode in contact with biological cells for providing electrical therapy to the biological cells, and wherein, upon commencement of the second proximity occurrence, the electronic circuits have been programmed to enter into magnet-mode so that either the AIMD discontinues providing electrical therapy to the biological cells or the AIMD enters into a preset therapy mode for providing electrical therapy to the biological cells, and wherein, upon commencement of the second proximity occurrence, the electronic circuits have been programmed to remain in magnet-mode for as long as the magnetic-detection sensor detects that the magnet is in close proximity to the AIMD.

The present invention further relates to an AIMD having electronic circuits that have been programmed to register when the magnetic-detection sensor detects that the magnet has either a north or a south polarity facing the AIMD as the first proximity occurrence, and wherein, within the defined first-time window upon commencement of the first proximity occurrence, the electronic circuits have been programmed to register when the magnetic-detection sensor no longer detects that the magnet is in close proximity to the AIMD as the first removal occurrence, and wherein, within the defined second-time window, the electronic circuits have been programmed to register when the magnetic-detection sensor detects that the magnet has been flipped so that the other of the north or the south polarity is in close proximity to the AIMD as the second proximity occurrence to thereby cause the electronic circuits of the AIMD to enter into magnet-mode.

The present invention also relates to an active implantable medical device (AIMD) comprising a housing for the AIMD, the housing containing a magnet-detection sensor connected to electronic circuits, wherein the electronic circuits have been programmed to register when the magnetic-detection sensor detects that a magnet is in close proximity to the AIMD as a first proximity occurrence, and wherein, within a defined first-time window of at least $n_1$ seconds to a maximum of $n_2$ seconds upon commencement of the first proximity occurrence, the electronic circuits have been programmed to register when the magnet-detection sensor no longer detects that the magnet is in close proximity to the AIMD as a first removal occurrence, and wherein, within a defined second-time window of at least $n_3$ seconds to a maximum of $n_4$ seconds upon commencement of the first removal occurrence, the electronic circuits have been programmed to register when the magnetic-detection sensor again detects that the magnet is in close proximity to the AIMD as a second proximity occurrence to thereby cause the electronic circuits of the AIMD to enter into magnet-mode, and wherein $n_1$ and $n_3$ seconds are the same or different and wherein $n_2$ and $n_4$ seconds are the same or different, and wherein, upon commencement of the second proximity occurrence, the electronic circuits have been programmed to remain in magnet-mode for as long as the magnetic-detection sensor detects that the magnet is in close proximity to the AIMD or wherein, instead of entering into magnet-mode upon commencement of the second proximity occurrence, the electronic circuits have been programmed not to enter into magnet-mode upon commencement of the second proximity occurrence, and wherein, within a third-time window of at least $n_5$ seconds to a maximum of $n_6$ seconds after commencement of the second proximity occurrence, the electronic circuits have been programmed to register when the magnetic-detection sensor no longer detects that the magnet is in close proximity to the AIMD as a second removal occurrence, and wherein, within a defined fourth-time window of at least $n_7$ seconds to a maximum of no second after commencement of the second removal occurrence, the electronic circuits have been programmed to register when the magnetic-detection sensor again detects that the magnet is in close proximity to the AIMD as a third proximity occurrence to thereby cause the electronic circuits of the AIMD to enter into magnet-mode, and wherein, upon commencement of the third proximity occurrence, the electronic circuits have been programmed to remain in magnet-mode for as long as the magnetic-detection sensor detects that the magnet is in close proximity to the AIMD.

The present invention also relates to a method for having an active implantable medical device (AIMD) enter into magnet-mode, the method comprising the steps of: providing an AIMD housing a magnet-detection sensor connected to electronic circuits, wherein the electronic circuits have been programmed to register when the magnetic-detection sensor detects a defined sequence when a magnet is moved in and out of close proximity to the AIMD to thereby cause the electronic circuits to enter into magnet-mode; providing a magnet of a defined Gauss; moving the magnet into close proximity to the AIMD so that the electronic circuits register when the magnet-detection sensor detects the magnet as a first proximity occurrence; then, within a defined first-time window after commencement of the first proximity occurrence, moving the magnet away from the AIMD so that the electronic circuits register when the magnet-detection sensor no longer detects the magnet as a first removal occurrence; and then, within a defined second-time window after commencement of the first removal occurrence, moving the magnet back into close proximity to the AIMD with the electronic circuits registering when the magnetic-detection sensor detects that the magnet is in close proximity to the AIMD as a second proximity occurrence, thereby causing the electronic circuits of the AIMD to enter into magnet-mode.

The method according to the present invention further includes programming the electronic circuits to remain in magnet-mode upon commencement of the second proximity occurrence for as long as the magnetic-detection sensor detects that the magnet is in close proximity to the AIMD, and providing the magnet having a strength of at least about 9 Gauss, and selecting the magnet-detection sensor from the group of a reed switch, a Hall-effect sensor and a giant magnetoresistive (GMR) sensor.

Further, the method of the present invention includes programming the electronic circuits so that the first-time window upon commencement of the first proximity occurrence has a duration of from 2 to 10 seconds, and so that the second-time window upon commencement of the first removal occurrence has a time duration of from 2 to 10 seconds.

An additional aspect of the present invention includes connecting the AIMD to a lead wire extending to a distal electrode in contact with biological cells for providing the electrical therapy to the biological cells, then, within the defined second-time window after commencement of the first removal occurrence, moving the magnet back into close proximity to the AIMD so that the magnetic-detection sensor again detects that the magnet is in close proximity to the AIMD as a second proximity occurrence, thereby causing the electronic circuits to enter into magnet-mode so that the AIMD either discontinues providing electrical therapy to the biological cells or enters into a preset therapy mode for providing electrical therapy to the biological cells, and further including programming the electronic circuits to remain in magnet-mode upon commencement of the second proximity occurrence for as long as the magnetic-detection sensor detects that the magnet is in close proximity to the AIMD.

Another aspect of the present invention includes programming the electronic circuits to register when the magnetic-detection sensor detects that the magnet has either a north or a south polarity facing the AIMD as the first proximity occurrence, and then, within the define first-time window after commencement of the first proximity occurrence, removing the magnet from being in close proximity to the AIMD so that the magnet-detection circuits no longer register that the magnet is in close proximity to the AIMD as the first removal occurrence, and then, within the defined second-time window after commencement of the first removal occurrence, flipping and moving the magnet into close proximity to the AIMD so that the magnet-detection sensor detects the other of the north and the south polarity of the magnet as the second proximity occurrence, thereby causing the electronic circuits of the AIMD to enter into magnet-mode, and further programming the electronic circuits to remain in magnet-mode upon commencement of the second proximity occurrence for as long as the magnetic-detection sensor detects that the magnet is in close proximity to the AIMD.

An alternate method according to the present invention includes programming the electronic circuits not to enter into magnet-mode upon commencement of the second proximity occurrence, further including: within a defined third-time window after commencement of the second proximity occurrence, moving the magnet away from the AIMD so that the magnet-detection sensor no longer detects the magnet with the electronic circuits having been programmed to register a second removal occurrence; and then, within a fourth-time window after commencement of the second removal occurrence, moving the magnet back into close proximity to the AIMD so that the magnet-detection sensor detects the magnet as a third proximity occurrence, thereby causing the electronic circuits of the AIMD to enter into magnet-mode, and programming the electronic circuits to remain in magnet-mode upon commencement of the third proximity occurrence for as long as the magnetic-detection sensor detects that the magnet is in close proximity to the AIMD or, programming the electronic circuits not to enter into magnet-mode upon commencement of the second proximity occurrence, so that within a defined second plus x-time window after commencement of the second proximity occurrence, moving the magnet away from the AIMD so that the magnet-detection sensor no longer detects the magnet as a first plus x removal occurrence; and then, within a second plus x+1-time window after commencement of the first plus x removal occurrence, moving the magnet back into close proximity to the AIMD so that the magnetic-detection sensor detects the magnet as a second plus x proximity occurrence, thereby causing the electronic circuits of the AIMD to enter into magnet-mode, and programming the electronic circuits to remain in magnet-mode after commencement of the second plus x proximity occurrence for as long as the magnetic-detection sensor detects that the magnet is in close proximity to the AIMD.

These and other aspects of the present invention will become increasingly more apparent to those of ordinary skill in the art by reference to the following detailed description and the appended drawings.

BRIEF DESCRIPTION OF THE DRAWINGS

FIG. 1N is a slide taken from a pacemaker manufacturer that illustrates what happens when a magnet is deliberately placed over a pacemaker.

FIG. 1O is an ICD magnet summary taken from a paper presented to the Heart Rhythm Society.

DETAILED DESCRIPTION OF THE PREFERRED EMBODIMENTS

Definition: time limitations or windows of each magnet placement over an AIMD or flip in the flow charts of the present invention are greater than one second but may be as long as hundreds of seconds. In a preferred embodiment, the time windows range from about 3 seconds to about 10 seconds. In an alternate embodiment, the time windows range from about 2 seconds to 20 about seconds. The clinical magnet placement timing and the timing between flips does not need to be precise and can simply embody the clinician counting in his head, or silently singing the words "happy birthday to you", and the like.

Figure 1:
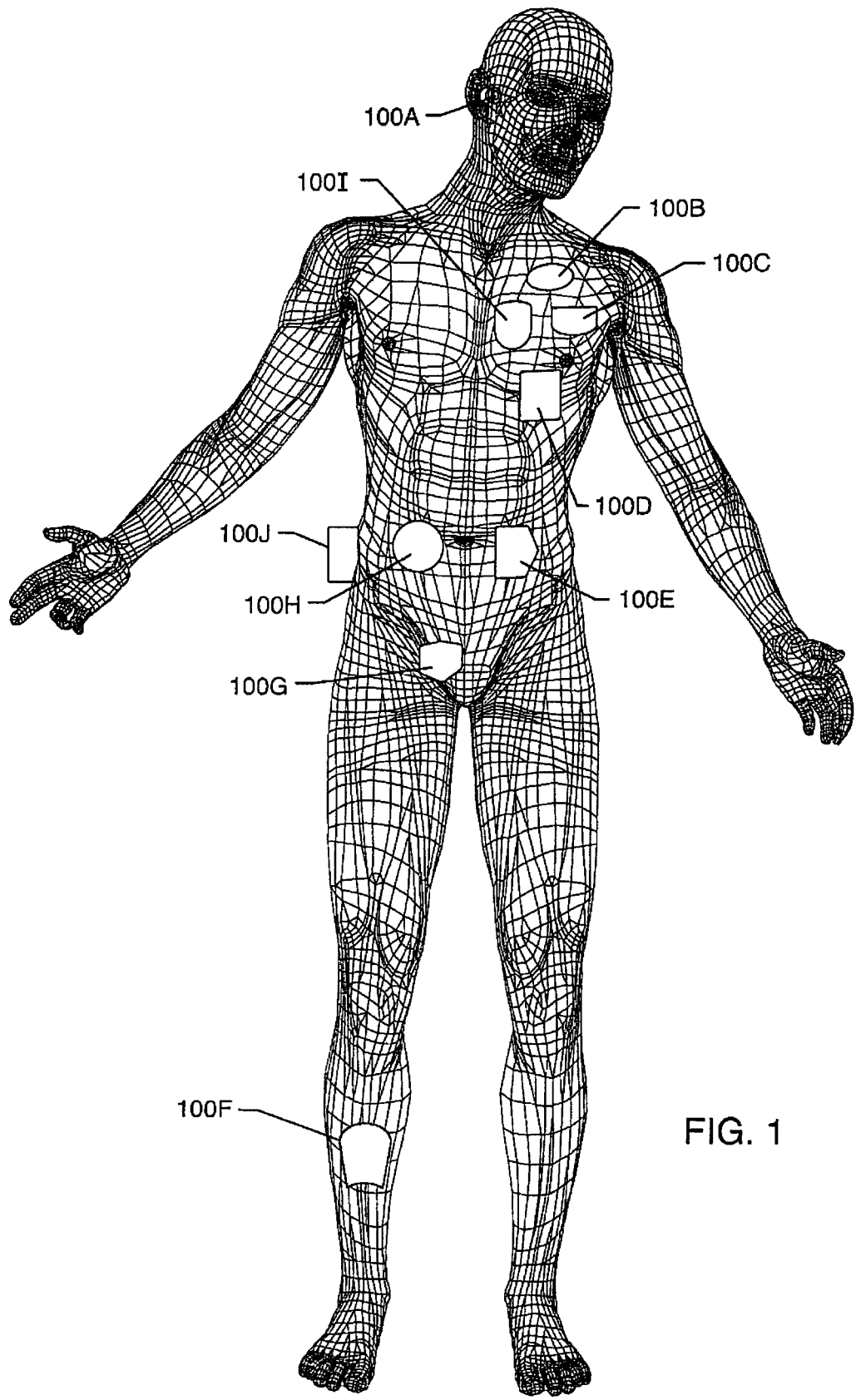
FIG. 1 is a wire-formed diagram of a generic human body showing a number of implanted medical devices.

Turning now to the drawings, FIG. 1 is a wire-formed diagram of a generic human body showing a number of implanted medical devices. Numerical designation 100A relates to a family of external and implantable hearing devices which can include the group of hearing aids, cochlear implants, piezoelectric sound bridge transducers, and the like.

Numerical designation 100B includes an entire variety of neurostimulators and brain stimulators. Neurostimulators are used to stimulate the Vagus nerve, for example, to treat epilepsy, obesity, and depression. A brain stimulator is similar to a pacemaker-like device in that it includes electrodes implanted deep into the brain for sensing the onset of a seizure and also for providing electrical stimulation to brain tissue to prevent a seizure from occurring. The leads that come from a deep brain stimulator are often placed using real time imaging. Most commonly such leads are placed during real time MRI imaging.

Numerical designation 100C relates to the family of cardiac pacemakers, which as is well-known in the art, may have endocardial or epicardial leads. Implantable pacemakers may also be leadless. The family of cardiac pacemakers 100C includes a cardiac resynchronization therapy device (CRT-D pacemakers) and a leadless pacemaker. A CRT-D pacemaker is unique in that it is designed to pace both the right and left sides of the heart. The family of cardiac pacemakers 100C also includes all types of implantable loop recorders or biologic monitors, such as a cardiac monitor. The illustrated cardiac pacemaker 100C could also be any type of biologic monitoring or data recording device including loop recorders, and the like.

Numerical designation 100D includes the family of left ventricular assist devices (LVAD's) and artificial hearts.

Numerical designation 100E includes the entire family of drug pumps, which can be used for dispensing insulin, chemotherapy drugs, pain medications, and the like. Insulin pumps are evolving from passive devices to active devices that have sensors and closed loop systems to monitor blood sugar levels in real time. Active drug pumps tend to be more sensitive to EMI than passive pumps that have no sense circuitry or externally implanted leads.

Numerical designation 100F includes a variety of external or implantable bone growth stimulators for rapid healing of fractures.

Numerical designation 100G includes urinary incontinence devices.

Numerical designation 100H includes the family of pain relief spinal cord stimulators and anti-tremor stimulators.

Numerical designation 100H also includes an entire family of other types of neurostimulators used to block pain.

Numerical designation 100I includes the families of implantable cardioverter defibrillator (ICD) devices and congestive heart failure devices (CHF). These types of devices are known in the art as cardio resynchronization therapy devices, otherwise known as CRT devices.

Numerical designation 100J illustrates an externally worn pack that could be an external insulin pump, an external drug pump, an external neurostimulator, a Holter monitor with skin electrodes or even a ventricular assist device power pack.

It is noted that numerical designation 100I is illustrated as an implantable defibrillator, which can have either endocardial or epicardial leads. This family also includes subcutaneous defibrillators.

It is also noted that some of the medical devices depicted in FIG. 1 can have both an implanted part and an externally worn part, such as the family of devices indicated with numerical designation 100J. Of particular concern from a human factor perspective are those implanted medical devices that can be implanted in a pectoral pocket area. These include those with numerical designations 100B, 100C, 100D, 100I and 100L.

Not shown in FIG. 1 is the human buttocks area, which is a common place to implant a spinal cord stimulator. Other common locations for implantation of AIMDs include the abdomen, or areas low in the groin.

Figure 1A:
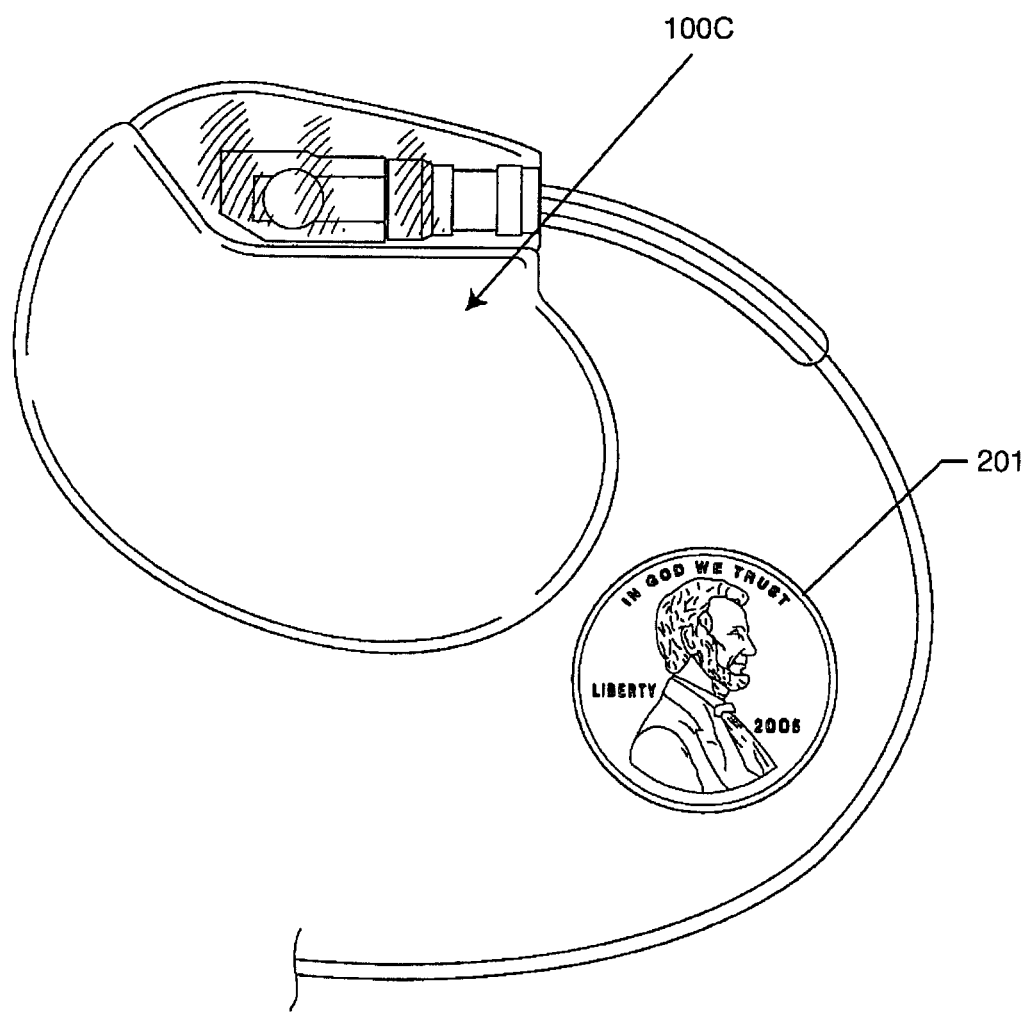
FIG. 1A illustrates the relative size of a cardiac pacemaker with respect to a U.S. penny (1-cent piece).
Figure 1B:
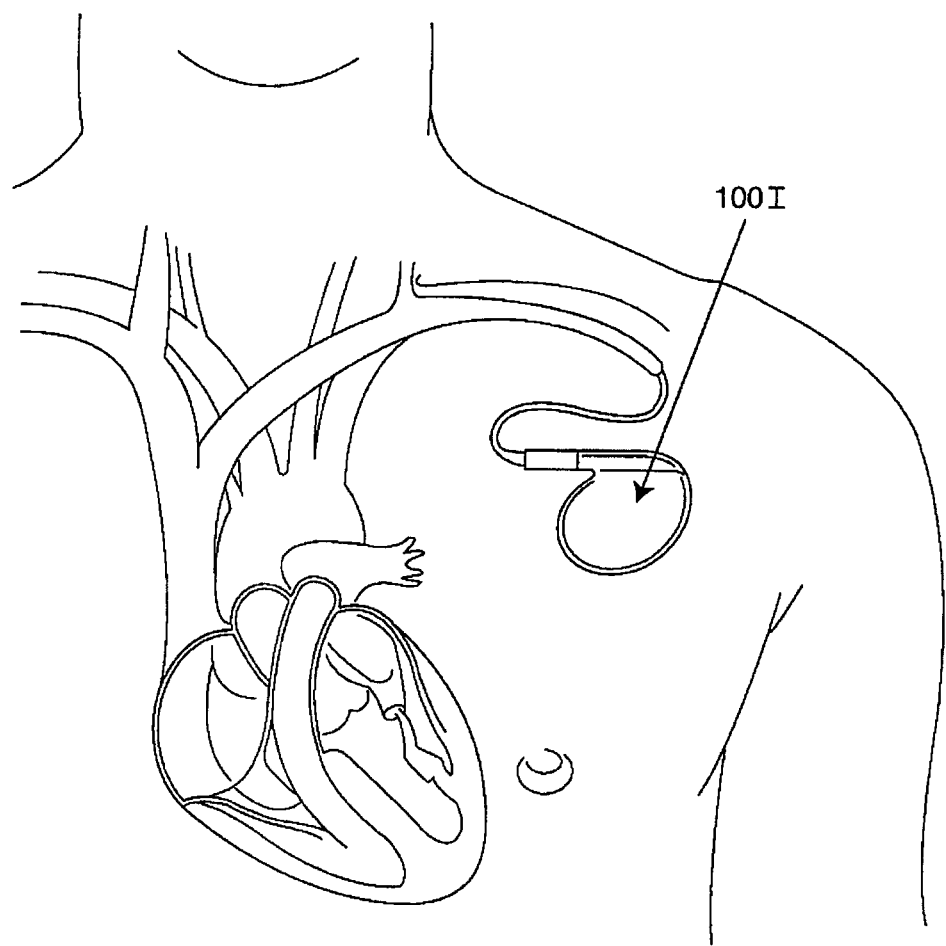
FIG. 1B illustrates the chest of a human patient with the outline of a dual chamber ICD 100I implanted subcutaneously.

FIG. 1B illustrates the chest of a human patient with the outline of a dual chamber ICD 100I implanted subcutaneously (sub-Q), which is most typical. Implant depth is important as the static magnetic field strength drops as an exponential function as the distance from the clinical magnet surface (or an inadvertent magnet) increases. Thin and elderly (thin skinned) patients with sub-Q implants are at the greatest risk of inadvertent magnet-mode response because their AIMD implant depth is typically relatively small (on the order of a few millimeters). Leads with distal electrodes are shown routed into endocardial tissue in the human heart. When a subcutaneous implant is performed, the implant depth from the skin surface is reduced. This makes the implanted device more susceptible to undesirably entering into magnet-mode when a portable electronic device, such as a cell phone with a charging alignment magnet is placed over the device, for example, in a shirt pocket. For perspective, the cardiac pacemaker 100C with leads is shown next to a U.S. penny 201 in FIG. 1A.

Figure 1C:
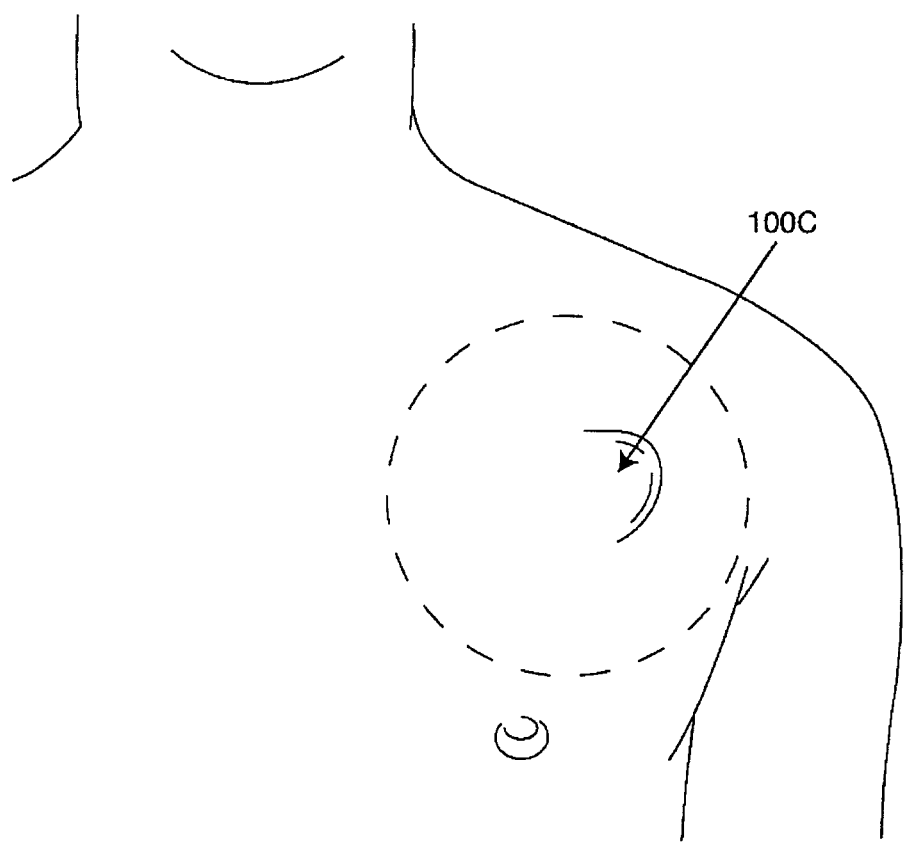
FIG. 1C shows a visible protruding lump in the patient's chest from the implantation of a pacemaker 100C.

FIG. 1C shows a visible protruding lump in the patient's chest from an older version of an implanted cardiac pacemaker 100C. Modern pacemakers are much thinner, making the pectoral implant more comfortable for the patient. However, a clinician can still palpate the area and feel the outline of the implanted pacemaker, which assists in deliberate placing of a pacemaker magnet. Spatial location of the magnet over the implanted pacemaker is important for activating magnet field sensors in the pacemaker or AIMD. Accurate spatial location over the implant is particularly important when the implant depth is deep. Elderly pacemaker patients, with a subcutaneous AIMD implant, generally have very thin skin, which means that the implant depth is not very deep. In that case, inadvertent AIMD magnet-mode entry, for example, by the ring magnet of an iPhone 12 becomes more likely because the distance between the phone and the subcutaneous implant is not very great (refer once again to Table 1). On the other extreme, a subpectoral muscle implant in a high body mass index (BMI) patient can result in the implant depth being several centimeters. In that situation, accurate spatial location becomes even more important.

Figure 1D:
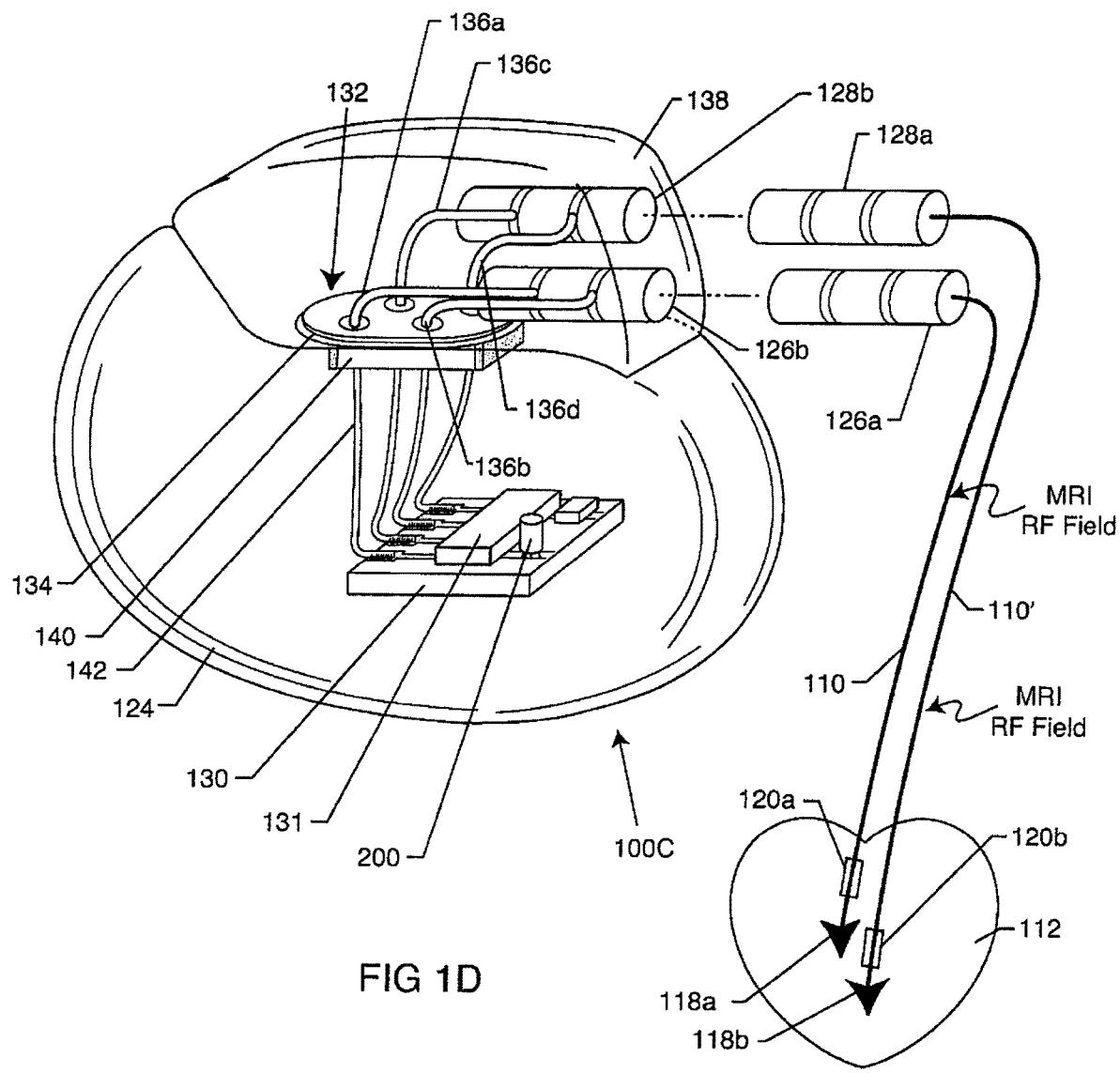
FIG. 1D illustrates a dual chamber cardiac pacemaker with its associated leads and electrodes implanted into a human heart.
Figure 6:
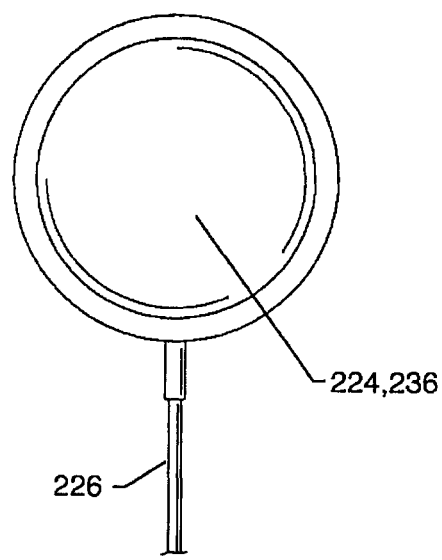
FIG. 6 illustrates an iPhone 12's MAGSAFE charging puck 224 for an iPhone 12 230.

FIG. 1D is taken from FIG. 6 of U.S. Pat. No. 10,561,837 and illustrates an AIMD, such as a cardiac pacemaker or ICD. The AIMD has a hermetically sealed housing 124 supporting a plastic or Tecothane® header block 138 into which leads 110 and 110' are plugged into and routed transvenously to electrodes located within the heart 112. The AIMD active electronic circuit board 130 is shown. It will be appreciated that this could be one circuit board or multiple circuit boards. Disposed on at least one AIMD circuit board is a programmable microprocessor 131, which can also be thought of as a minicomputer.

Numerical designation 200 indicates a static magnetic field detector such as a reed switch, a Hall-effect sensor or a GMR sensor. These are just three examples of many types of static and/or time varying magnetic field sensors that may be used in AIMDs (or in the future may be). The present invention also covers emergent or new technologies yet to be discovered in the field of static magnetic field sensors. Importantly, the static magnetic field sensor at a minimum detects the presence of a clinical magnet and provides an output that can be used in new AIMD programming as describe herein. In a preferred embodiment, the AIMD magnetic field sensor both detects the presence of a clinical magnet and also its north-south or south-north polarity.

FIG. 1D is a pectoral view of a cardiac pacemaker 100C showing dual chamber bipolar leads 110, 110' routed to distal tip electrodes 118a and 118b and distal ring electrode 120a and 120b. As can be seen, the leads 110, 110' are exposed to a powerful RF-pulsed field from an MRI machine. This induces electromagnetic energy on the leads which are coupled via ISO Standard IS-1 or DF-1 connectors 126a/126b, 128a/128b through header block 138 which connect the leads to electronic circuits supported on a circuit board 130 inside the hermetically sealed device housing 124. A hermetic seal assembly 132 is shown with a metal ferrule 134 which is generally laser welded into the titanium housing 124 of the cardiac pacemaker 100C. Lead wires 136a through 136d penetrate the ferrule 134 of the hermetic seal in non-conductive relation. Glass seals or gold brazed alumina insulators are formed to make the hermetic seal which keeps body fluids from getting to the inside of the pacemaker housing 124. Also shown is a rectangular quadpolar feedthrough capacitor (planar array) 140 mounted to the hermetic terminal 132. All of the element numbers in FIG. 1D are the same as the element numbers in U.S. Pat. No. 10,561,837, the contents of which are herein incorporated fully by reference.

Referring once again to FIG. 1D, a static magnetic field sensor 200, such as a reed switch, a GMR sensor, a Hall-effect sensor, anisotropic/giant/tunnel magneto-resistance sensor is supported on the circuit board 130 housed inside the AIMD. The magnetic field sensor is designed to sense the magnetic field when a clinical magnet is purposely placed over the device, for example, when it is desired to have the device enter into magnet-mode at a predetermined static magnetic field strength.

Figure 1E:
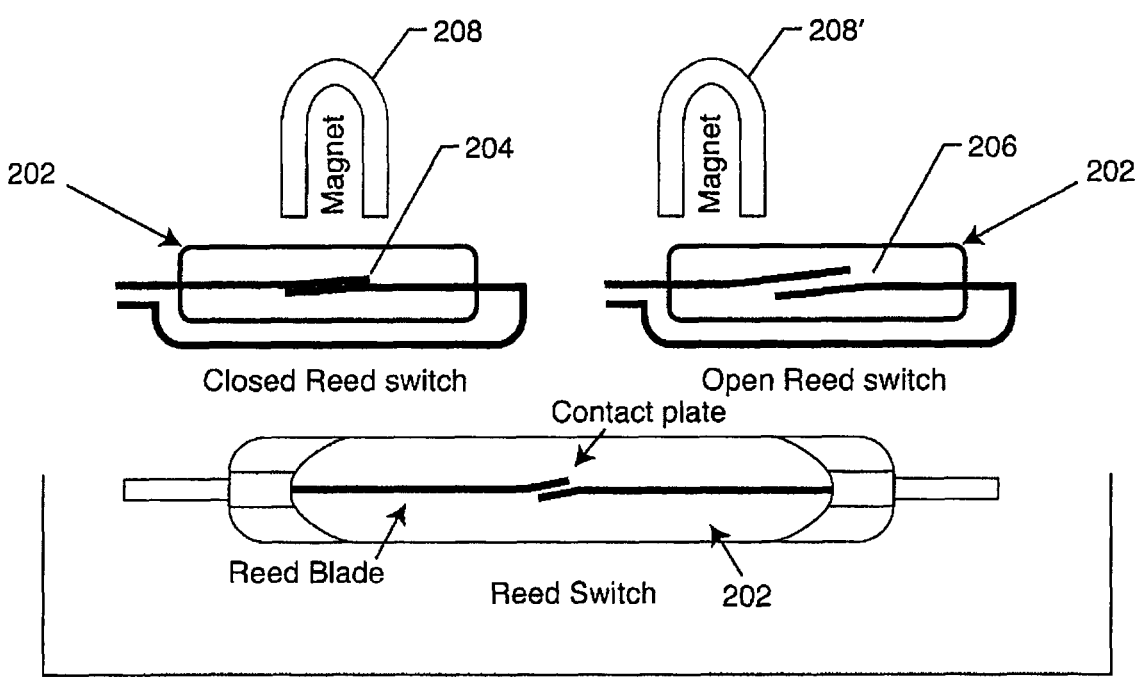
FIG. 1E illustrates a reed switch 202 in an open position and a closed position.

FIG. 1E illustrates a typical reed switch 202 having internal mechanical contact plates and reed blades. Application of a magnet 208 directly over the reed switch 202 causes contact 204 to close. When the magnet 208' is misaligned or not directly over the reed switch 202, however, the switch remains open 206. Today, some AIMDs still use a reed switch, but many now use Hall-effect or equivalent sensors 200, including those that are described in U.S. Pat. No. 8,600,505 (FIG. 1D).

A Hall-effect sensor 200 is a device used to measure the magnitude of a magnetic field. Its output voltage is directly proportional to the magnetic field strength through it. Frequently, a Hall-effect sensor is combined with a threshold detector so that the sensor acts as a switch. When a Hall-effect sensor 200 acts as an electronic switch, there are important advantages. A Hall-effect switch costs much less than a mechanical switch (including a Reed switch 202) and is much smaller and more reliable. Further, a Hall-effect sensor operates at much higher frequencies than a mechanical switch and because it is a solid-state switch, it typically does not suffer from contact bounce. The Hall-effect sensor 200 (FIG. 1D) can measure both the polarity and amplitude of a wide range of static magnetic fields (no current AIMD takes advantage of this ability to sense polarity). The Hall-effect sensor 200 can have many shapes including flat. Additionally, a reed switch 202 has a binary on/off threshold of some variability whereas a Hall-effect sensor 200 produces a continuous output of excellent precision and accuracy.

Figure 1F:
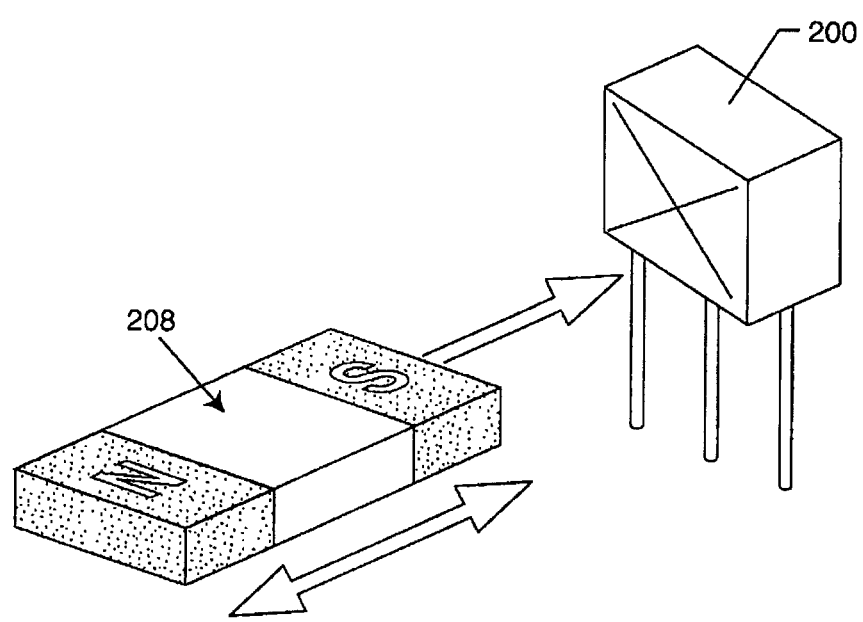
FIG. 1F illustrates a bar magnet 208 being brought into relatively close proximity to a Hall-effect sensor 209.

FIG. 1F illustrates a bar magnet 208A being brought into relatively close proximity to a Hall-effect sensor 200. At a predetermined level of static magnetic field strength, circuitry in the Hall-effect sensor 200 produces an output voltage which triggers other AIMD circuitry to enter magnet-mode. In general, this predetermined static magnetic field strength level is programmable.

Figure 1G:
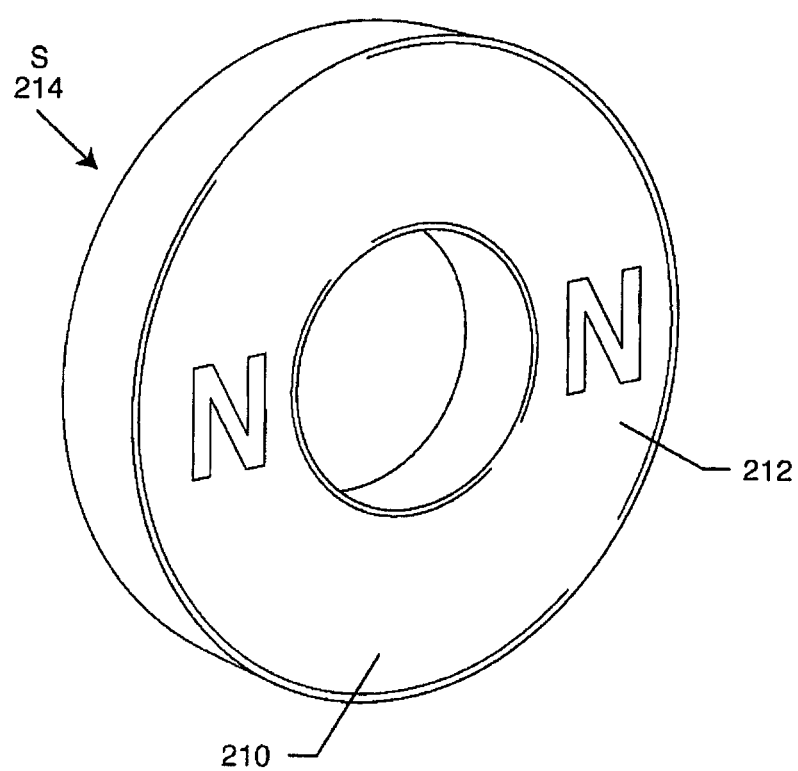
FIG. 1G illustrates a typical clinical magnet 210 that is used to place an AIMD, such as a pacemaker or ICD into magnet-mode.

FIG. 1G illustrates a typical pacemaker or ICD magnet 210 in a donut or toroidal shape. As an example, the magnet facing side is marked with the static magnetic polarity "north" 212. Clinical magnets do not have north-south labelling on them. The opposite side of the magnet 210, which cannot be seen, is marked with the static magnetic polarity "south" 214. The purpose of this magnet is to position it over an AIMD to place the AIMD into its magnet-mode (without regard to polarity). Generally, such existing clinical magnets 210 have a field strength of about 70 to 120 Gauss with a minimum field strength, in accordance with ISO 14117, of 9 Gauss. The static magnetic field strength of a magnet, in Gauss, depends on whether the measurement is taken at the face of the magnet or some distance away from the face. This is why the reference to ISO 14117, which has a specific method of measuring Gauss. ISO 14117 specifies that a clinical magnet shall not induce magnet-mode at a field strength less than 9 Gauss.

There are hundreds of thousands, if not millions, of these types of clinical magnets scattered throughout the world from clinics (including in third world countries) to major hospitals to emergency rooms. A major purpose of the present invention is to find an effective way to safely use these existing clinical magnets to activate the magnet-mode in an AIMD. Clinical magnets are not marked with a north or south polarity nor is any commercially available AIMD enabled or programmed to detect the north-south polarity of a clinical magnet.

Figure 1H:
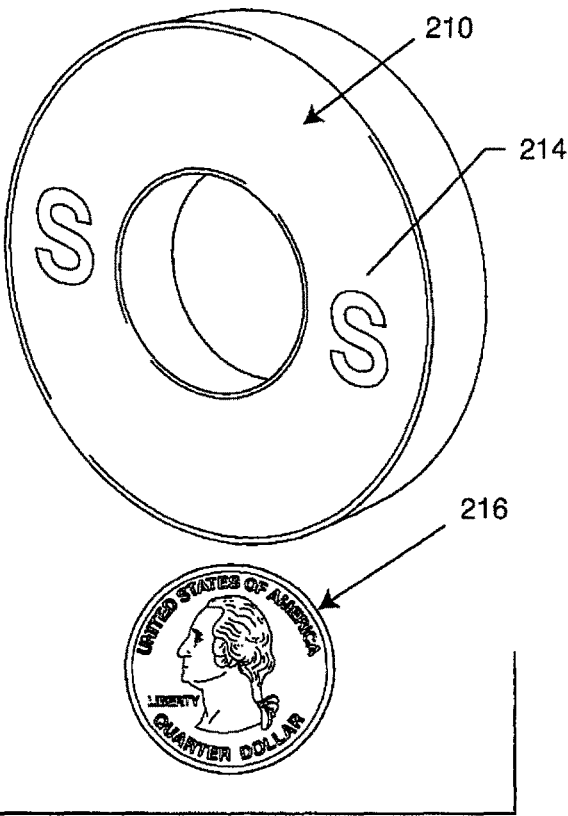
FIG. 1H illustrates the south face of the magnet 210 shown in FIG. 1G next to a U.S. quarter 216 (25-cent piece) for size comparison.

FIG. 1H illustrates the south face of the magnet 210 next to a U.S. quarter 216 (25-cent piece) for size comparison. FIG. 1H also describes what happens when a relatively strong magnet 210 is placed directly over a conventional pacemaker. As indicated, the magnet 210 will switch the pacemaker to an asynchronous magnet-mode. As previously discussed, prolonged asynchronous pacing can lead to reduced hemodynamic output, premature battery depletion, and a rare but very dangerous R-T event, which can induce immediate life-threatening ventricular fibrillation (VF).

Figure 1I:
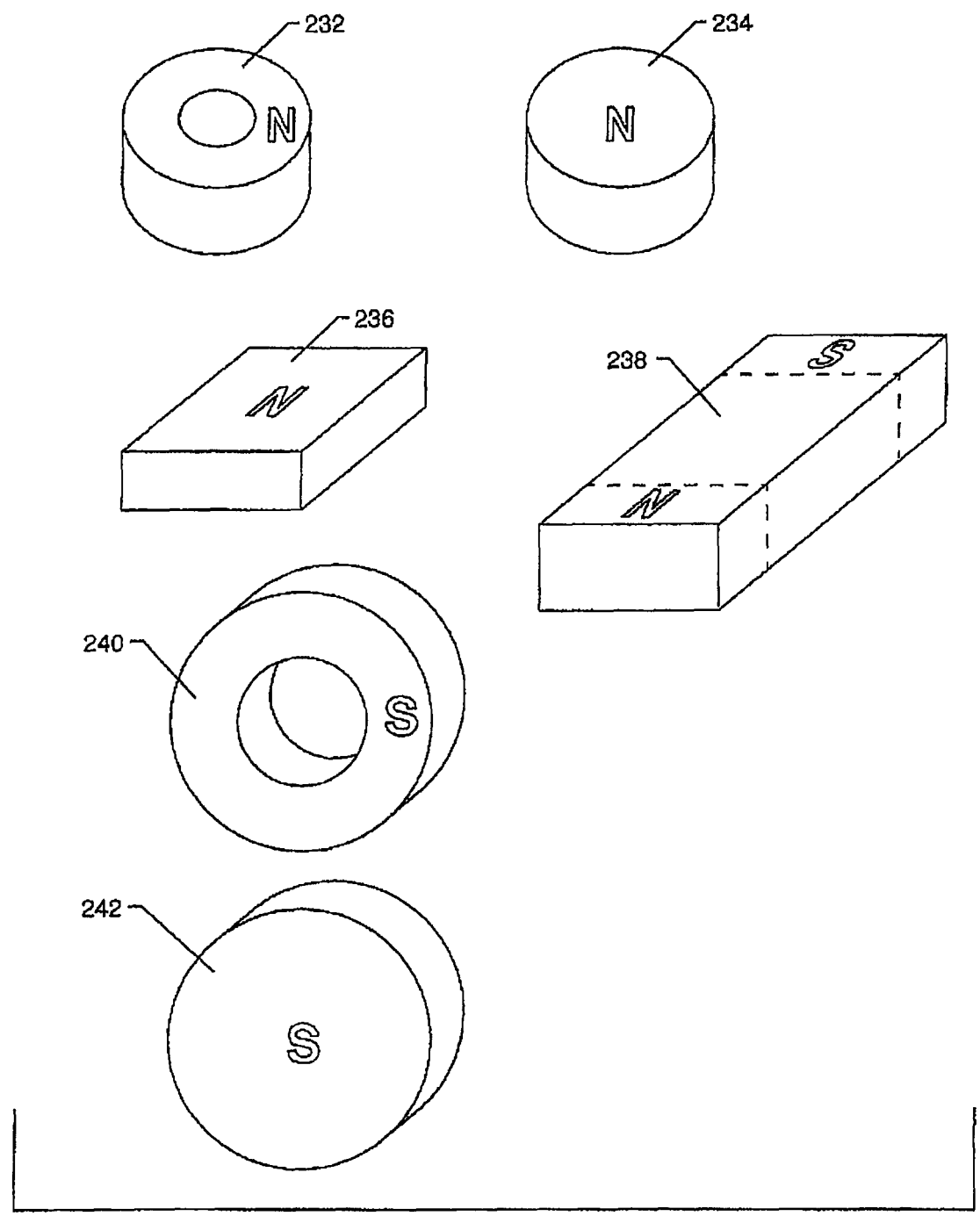
FIG. 1I illustrates various donut-shaped or toroidal-shaped clinical magnets 210, 232, 234, 236, 238, 240 and 242 that are designed to cause an AIMD to enter into its magnet-mode.

FIG. 1I illustrates that clinical magnets 210, 232 designed to put an AIMD into magnet-mode can also be donut-shaped or toroidal, solid round magnets 234, square magnets 236 or even rectangular magnets 238. It will also be appreciated that the magnets can even be elliptical with a center hole or solid ellipses 242. In other words, the present invention is not constrained by any particular magnet shape.

Figure 1J:
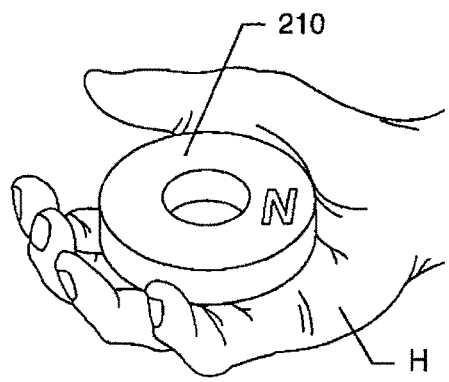
FIG. 1J shows the clinical magnet 210 of FIG. 1H in the hand of a clinician who is about ready to place it over the patient's AIMD.

FIG. 1J shows the clinical magnet 210 in the hand H of a clinician before placing the magnet over the patient's AIMD.

Figure 1K:
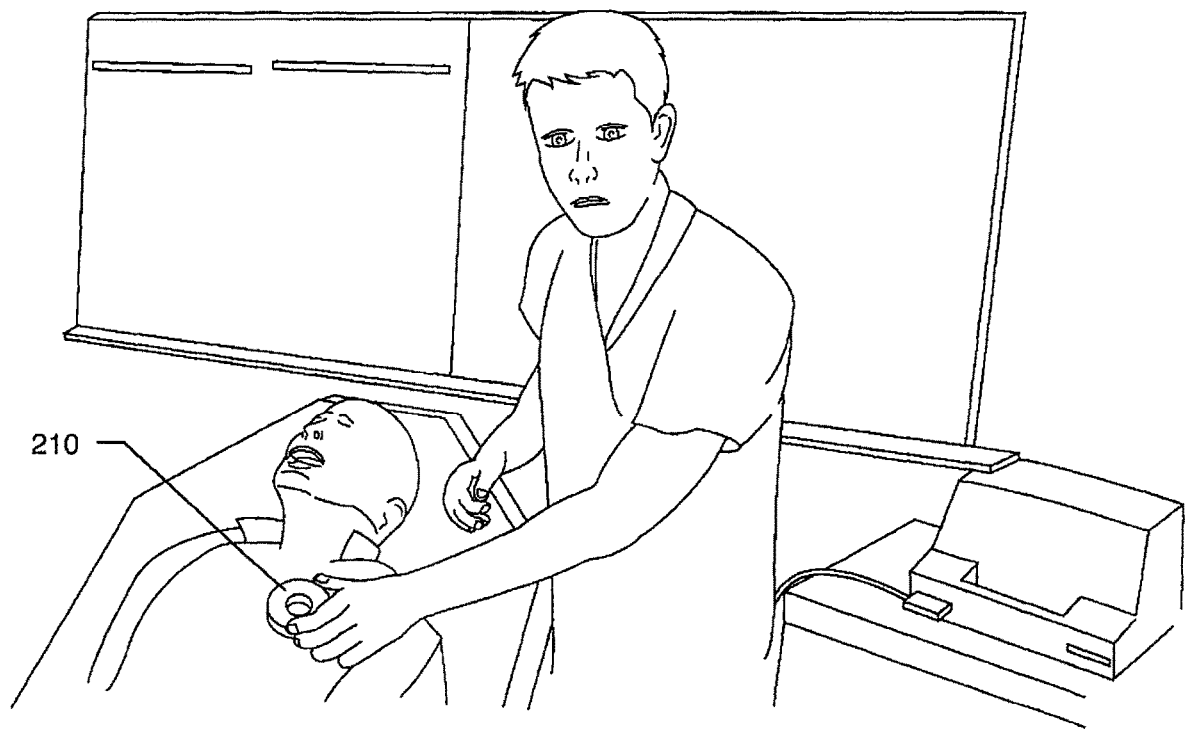
FIG. 1K shows a clinician properly placing the clinical magnet 210 of FIG. 1H over a patient's AIMD in a pectoral pocket area.

FIG. 1K shows the clinician properly placing the clinical magnet 210 over a patient's AIMD that is implanted in a left-chest pectoral pocket area.

Figure 1L:
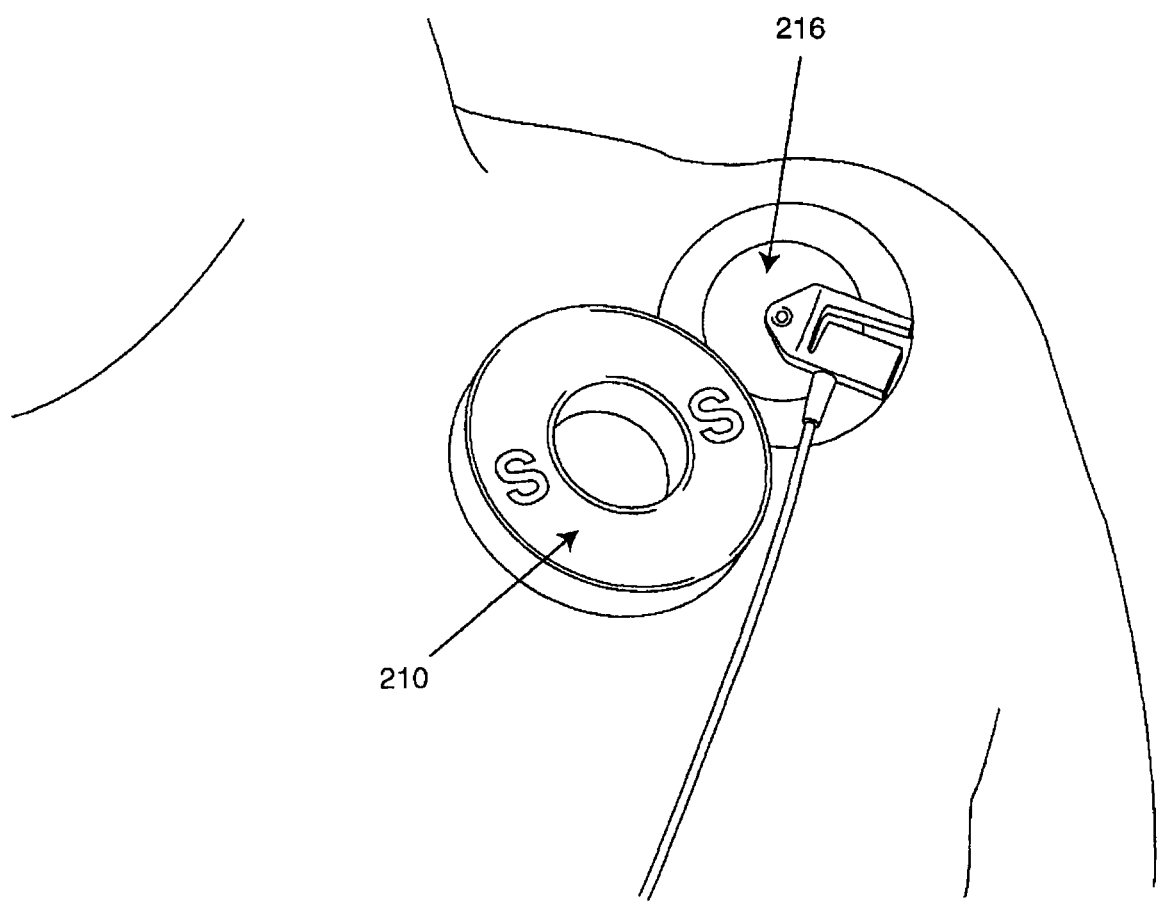
FIG. 1L shows the clinical magnet 210 of FIG. 1H being placed over a CIED, such as a cardiac pacemaker or ICD and an EKG electrode 216, which is monitoring cardiac waveforms.

FIG. 1L is a close-up of the magnet 210 being placed over the AIMD. Also shown is an EKG electrode 216, which is designed to monitor cardiac waveforms.

Figure 1M:
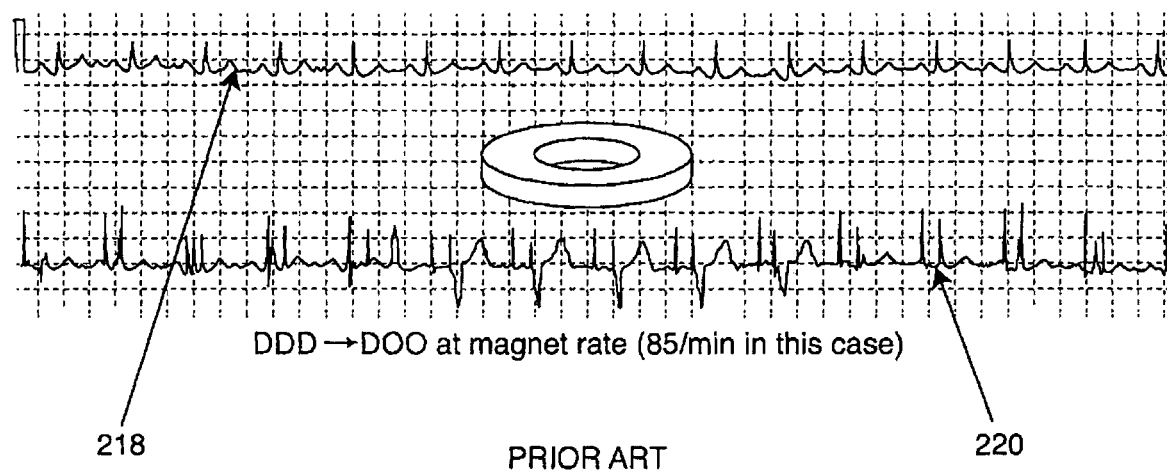
FIG. 1M illustrates that the patient shown in FIGS. 1J and 1K is in normal sinus rhythm 218 and after placement of the clinical magnet 210 of FIG. 1H, asynchronous fixed-rate pacing 220 occurred.

FIG. 1M illustrates that this particular patient was in normal sinus rhythm 218 and after placement of the clinical magnet 210, asynchronous pacing 220 occurred. One can see that the patient is now experiencing competitive pacing where the pacemaker is causing the heart to beat asynchronously with the patient's normal sinus heart rhythm. Pacemakers are generally used to treat bradycardia (slow heart rate). If this patient were in a bradycardic condition, that would mean the patient did not have an underlying sinus rhythm and there would be no potential for rate competition. However, the vast majority of bradycardic patients are not in bradycardia all the time. They may become bradycardic once or twice a month or at certain times in a day. Consequently, prolonged and inadvertent placement of a strong magnet (for example, the iPhone 12 ring magnet) can lead to the illustrated rate competition scenario 220. Unintended and prolonged rate competition is not healthy as the heart beats with an out of synchronization chaotic rhythm.

FIG. 1N is a slide taken from a pacemaker manufacturer that illustrates what happens when a magnet is deliberately placed over a pacemaker. One of the bullet points says, "Caution: asynchronous rate may not always meet the physiologic demands of the patient."

FIG. 1O is an ICD magnet summary taken from a paper presented to the Heart Rhythm Society. As one can see, there are variations in magnet-mode between ICD manufacturers, but one thing is constant with every manufacturer and that is in response to a deliberately placed magnet—ICD high voltage shock therapy is inhibited until the magnet is removed. As previously described, inadvertent suspension of high-voltage therapy, particularly for a prolonged period of time, means that the ICD is not able to respond to a life-threatening arrythmia, such as ventricular fibrillation. In other words, life-saving high-voltage shock therapy, in the presence of the magnet, is not possible.

Figure 2:
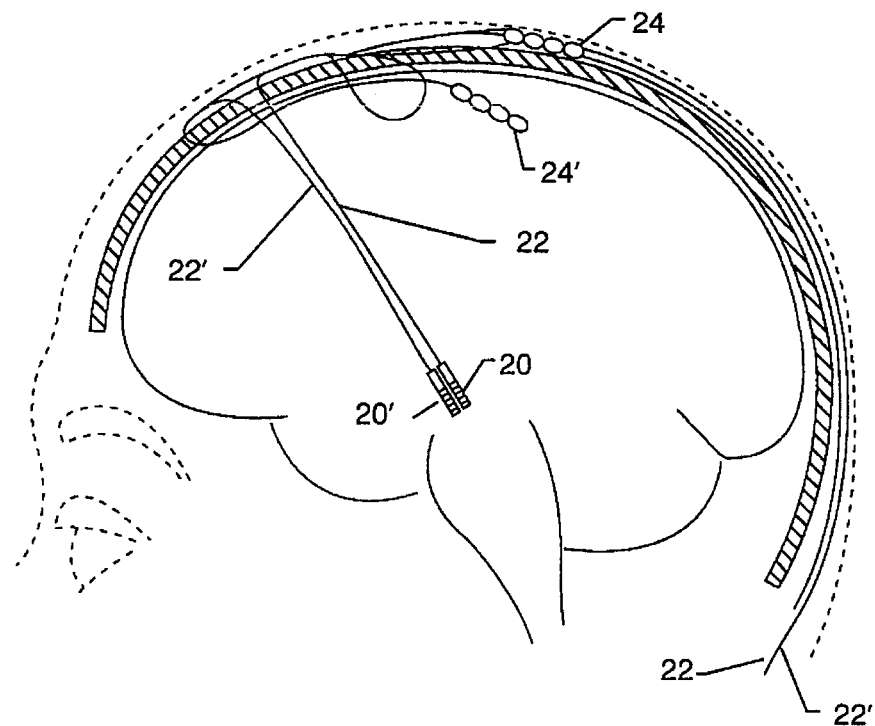
FIG. 2 is a is a side view of a human skull with two quadpolar brain stimulation electrodes placed deeply into brain matter.
Figure 3:
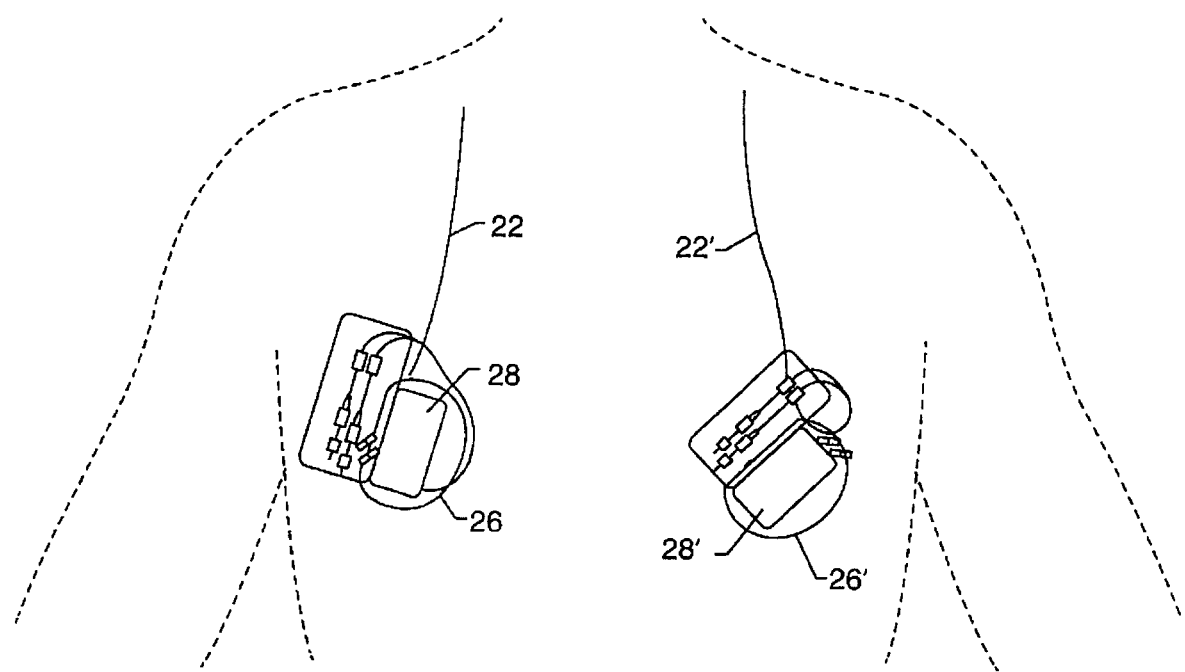
FIG. 3 is an X-ray tracing of the front view of the pectoral area of the same patient shown in FIG. 2, showing two implantable deep brain stimulator pulse generators 26 and 26'.

FIGS. 2 and 3 are taken from FIGS. 1 and 2, respectively, of U.S. Pat. No. 8,792,987. The element numbers depicted on FIGS. 2 and 3 are taken directly from the '987 patent, which is herein incorporated fully by this reference. Referring first to FIG. 2, one can see deep brain electrodes 20 and 20' that stimulate a particular area of the human brain to treat systems, such as Tourette's syndrome or Parkinson's Disease. These deep brain devices may have a magnet-mode which in most cases is used to suspend therapy (particularly during surgery when a clinical magnet is taped in place).

FIG. 3 indicates that the leads 22 and 22', in this case, are tunneled down to an implantable medical device or a deep brain stimulator (DBS), as shown on either the left or the right side (or both), in a pocket that the surgeon creates in the pectoral area. In general, cardiac devices, such as pacemakers and ICDs, and deep brain stimulator or even Vagus nerve stimulators (for epilepsy) can be implanted into the pectoral area either subcutaneously (meaning near the skin surface) or subpectorally (which means under the pectoral muscle). The types of implants that would be most at risk for undesirable placement of a magnet over them would be ones that are implanted subcutaneously, otherwise known as sub-Q. That is because the implant is much closer, for example, to a cell phone placed in a shirt pocket. The static magnetic field from a fixed magnet drops or decreases as the distance from the magnet increases. So, close proximity to the implant is a major concern.

Figure 4:
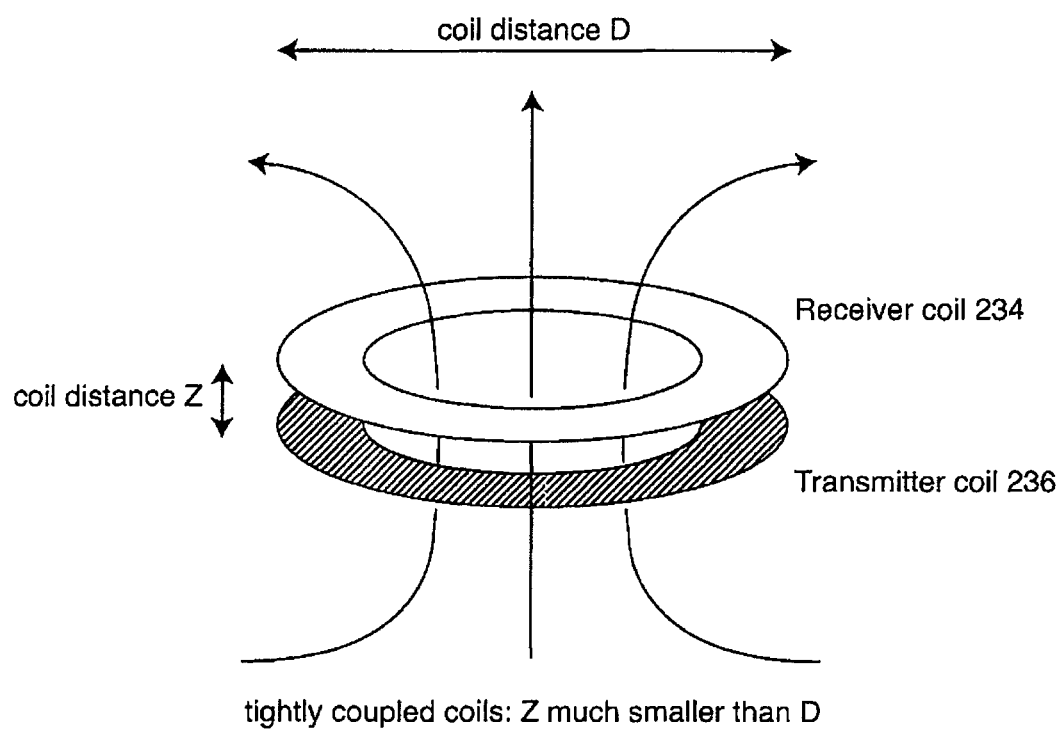
FIG. 4 is a diagram showing how wireless cell phone charging works.

FIG. 4 is a diagram showing how wireless cell phone charging works. A transmitter coil 236 generates a pulsing electromagnetic field. For electric vehicle charging, these are generally in the range of 15 to 25 kilohertz. For wireless charging of a cell phone, this might be in the range of 80 to 300 kilohertz. The present invention is directed to a much broader frequency range generally from 10 to 500 kilohertz. The transmitter coil 236 produces a pulsing electromagnetic field wherein a closely spaced receiver coil 234 picks up this energy, similar to how a transformer works. The receiver coil 234 is disposed inside the active implantable medical device (AIMD) and the transmitter coil 236 is connected to a charging wand, a charging puck 224 (FIGS. 6 and 7), a charging station, a charging desktop, and the like.

Importantly, the receiver coil 234 and the transmitter coil 236 need to be tightly or strongly coupled. In other words, distance Z, which is the spacing between the receiver and transmitter coils 234, 236 must be smaller than D, which is the diameter of the coils. Optimal transmission (energy coupling) occurs when the transmitter coil 236 has the same geometry and the same diameter as the receiver coil 234. The receiver coil 234 is generally connected to an electronic circuit that converts the AC signal that is received to a DC signal to thereby recharge the battery of the portable electronic device, including a cell phone, such as the iPhone 12 230. Optimal energy transfer occurs when the transmitting coil 236 is spatially aligned with the receiver coil 234, which is one purpose of the magnet in devices such as the iPhone 12. Another purpose of the magnet is magnetic adherence to the charging puck or wand such as a MAGSAFE® charging device. (MAGSAFE is a registered trademark of Apple Inc., Cupertino, CA) Another purpose of the magnet in a portable electronic device, such as a cell phone, is so that the transmitting station can sense the magnet field and activate itself, in other words, start transmitting.

Figure 5:
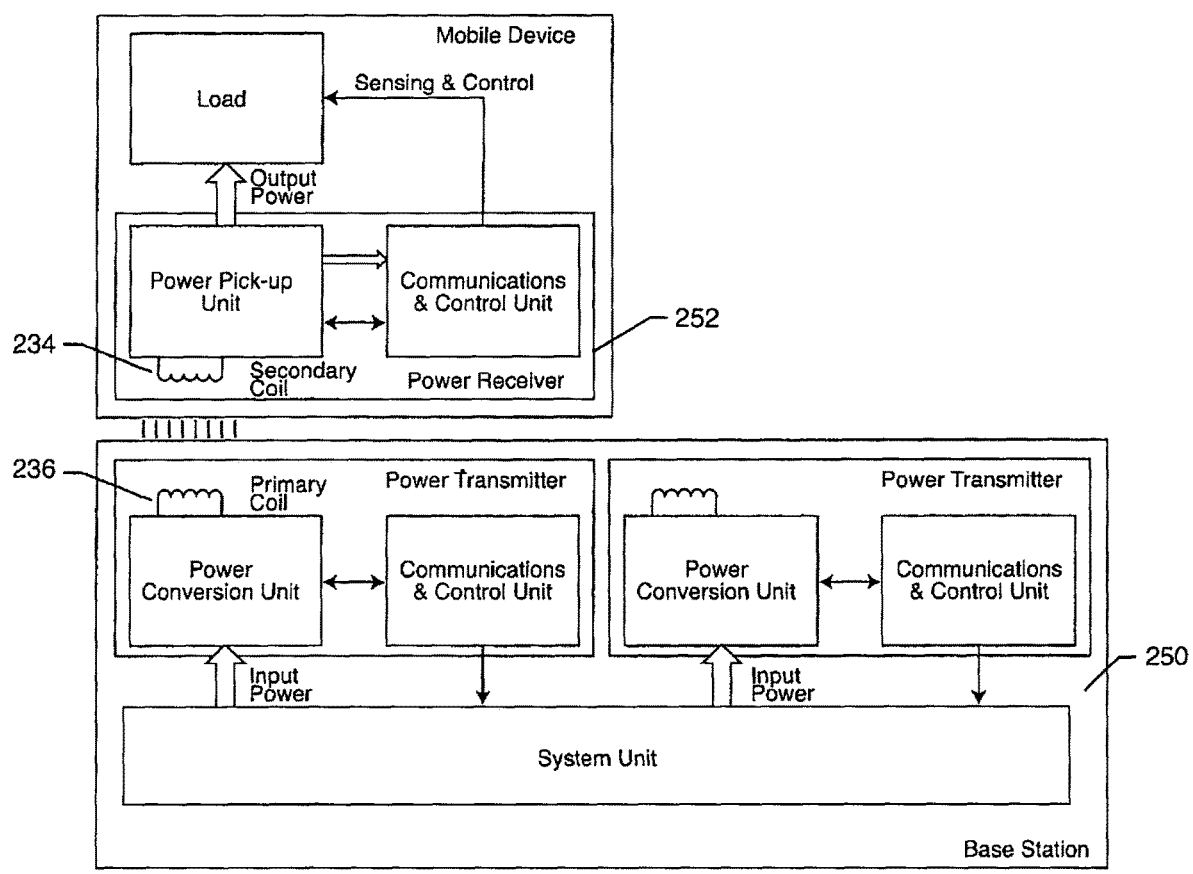
FIG. 5 is a is a diagrammatic representation of a base station 250 wirelessly coupled to a power receiver 252.

FIG. 5 is a diagrammatic representation of a base station 250 wirelessly coupled to a power receiver 252, which can be a mobile device such as a cellular phone. RF coupling is represented by facing coils 234, 236 of the base station 250 and the power receiver 252. Think of the base station 250 as the desktop or the center console of an automobile or the wand/puck of the iPhone 12 that creates the pulsing electromagnetic field picked up by the secondary coil in the power receiver (iPhone 12) in the mobile or portable device, such as a cellular phone.

FIG. 6 illustrates an iPhone 12's MAGSAFE® charging puck or wand 224. Inside this charging puck 224 is the transmitting coil 236 for wireless charging. The charging puck 224 has wires 226 shown at the bottom, which must be connected to an energy source (the base station 250 such as shown in FIG. 5). The base station 250 is connected to an energy source, for example, an AC wall plug or a box that plugs into a wall plug with a USB jack. With this MAGSAFE® wireless charging system, there is no need for any wires to be connected directly to the iPhone 12 to recharge its internal battery (this is why it is called wireless charging). The charging puck 224 has an embedded transmitting coil 236, as previously described in FIG. 4.

Figure 7:
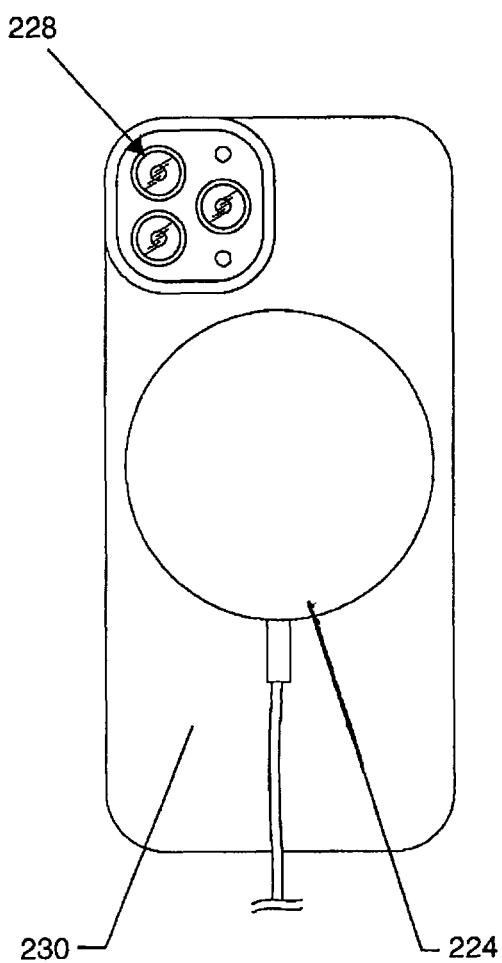
FIG. 7 is a photograph showing the back of the iPhone 12 with the MAGSAFE charging puck 224 shown in FIG. 6 magnetically adhered to the phone.
Figure 8A:
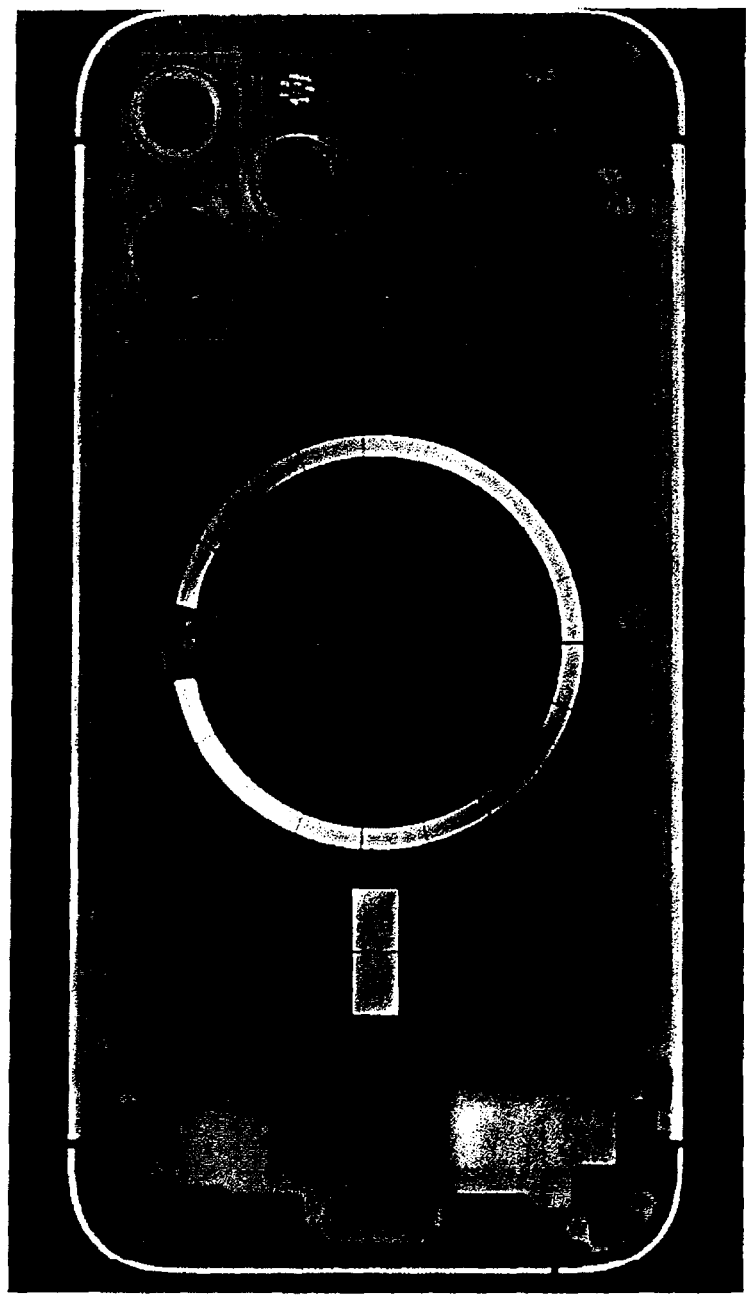
FIG. 8A is a CT scan showing that the ring magnet 232 of an iPhone® 12 has a diameter that is a significant portion of the width of the phone and similar to the diameter of a clinical magnet
Figure 8B:
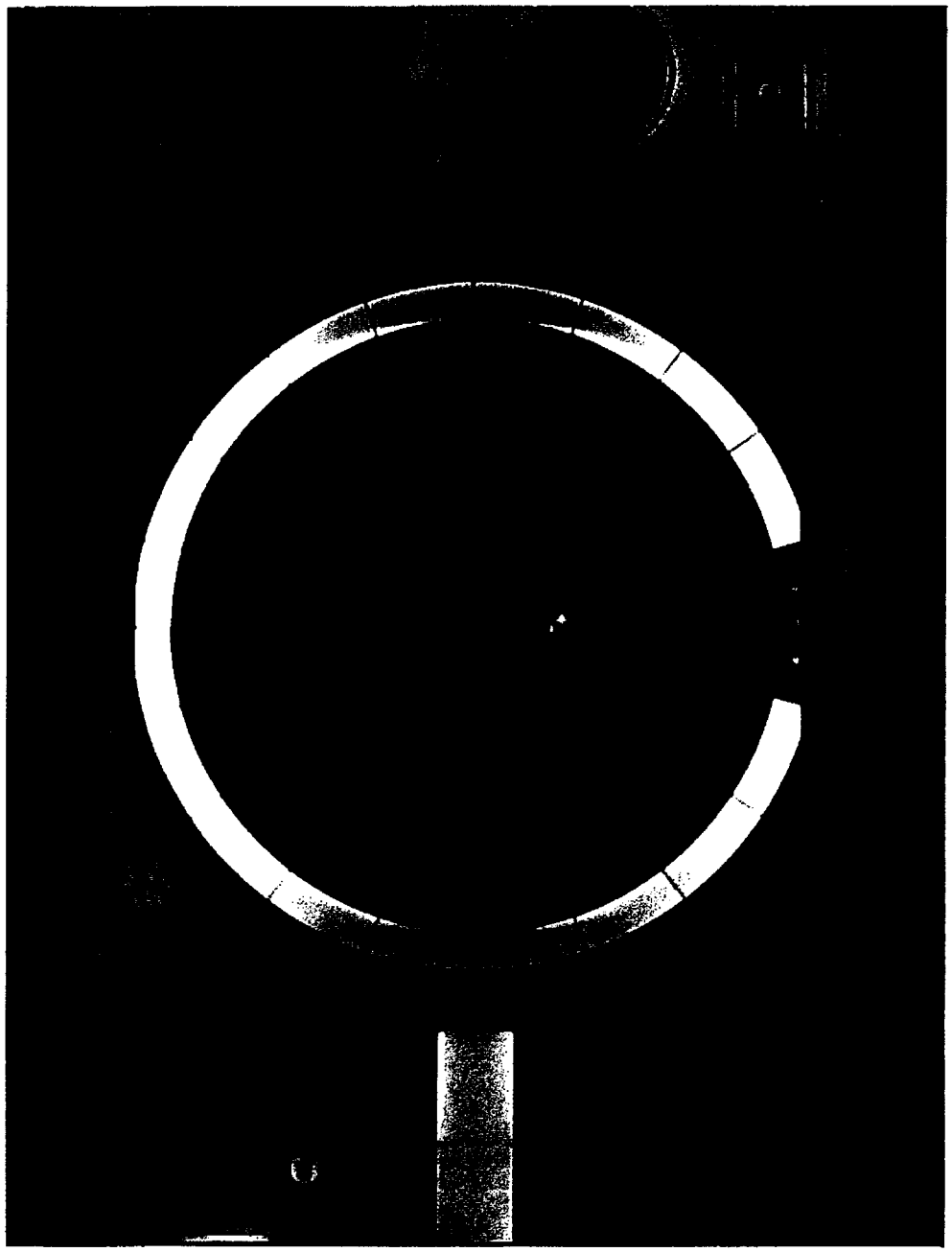
FIG. 8B is a CT scan of an iPhone 13 showing that the phone has a ring magnet that is very similar to the ring magnet of an iPhone 12.

FIG. 7 shows an iPhone 12 with the MAGSAFE charging puck 224 magnetically adhering to the back of the phone. Importantly, for maximum and efficient wireless charging and energy transfer, it is desirable that the transmitter coil 236 and the receiver coil 234 be spatially aligned as shown in FIG. 4. When the receiver coil 234 is significantly off-center from the transmitter coil 236, energy transfer is significantly reduced. Then little to no energy is transferred and the battery of the portable or body worn device will either be charged inefficiently or not charged at all. Referring to FIGS. 8A and 8B, there is a ring magnet 232 inside of the iPhone 12 and iPhone 13 that corresponds either to the magnet or a ring steel plate in the charging puck 224 so that the transmitter coil 234 and receiver coil 236 (FIG. 5) are magnetically adhered and spatially aligned.

Figure 8C:
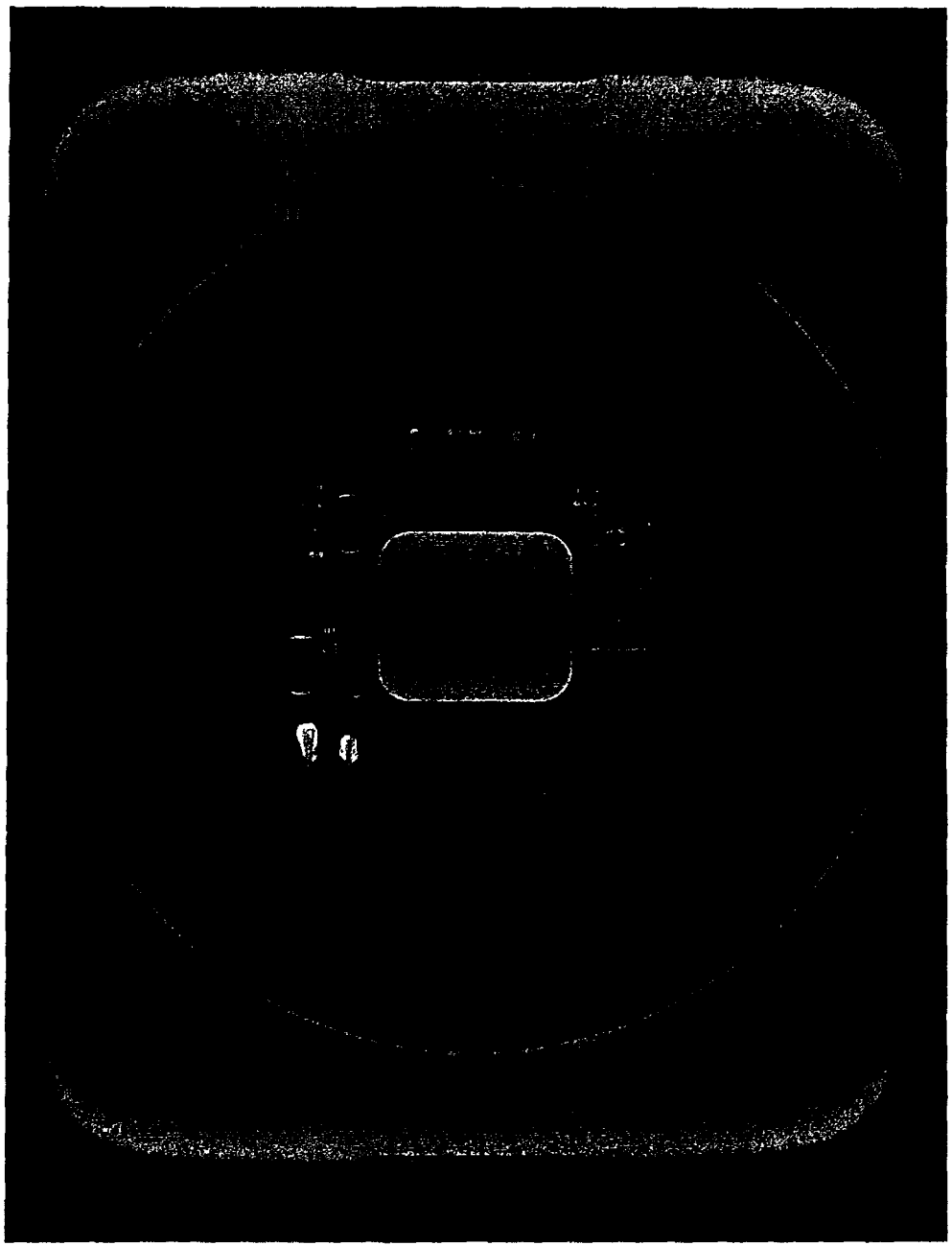
FIG. 8C is a CT scan of an Apple watch showing that the watch has a solid rectangular magnetic.

Referring now to FIGS. 8A, 8B and 8C, high-resolution computerized tomography (CT) scans of an iPhone 12, iPhone 13 and an Apple watch, respectively, were obtained so that their circuits, magnets and coils could be clearly and accurately visualized. FIGS. 8A and 8B show that the ring magnet 232 of the iPhone 12 and iPhone 13 have a diameter that is a significant portion of the width of the phone. Such a ring magnet 232 helps the iPhone 12 and iPhone 13 adhere and spatially align its receiver coil 234 with a transmitter coil 236. The transmitter coil 236 is ideally centered within the ring magnet. Unfortunately, such a large diameter ring magnet can create a large "sweet spot" over an implanted AMID magnet field sensor, which can enable prolonged inadvertent magnet mode response, which can be dangerous.

FIG. BB is a high-resolution CT scan of an iPhone 13 showing that it also has a ring magnet similar to the iPhone 12. In the case of the iPhone 13, the ring magnet appears to be even larger in diameter than the ring magnet of the iPhone 12.

FIG. 8C illustrates a powerful (refer again to Table 1) solid rectangular magnet inside the back of an Apple watch to facilitate spatial alignment and magnetic adherence to a base station or a charging puck 224.

In that respect, the present invention describes a new programming method using AIMD microprocessor firmware or software for inducing an AIMD into magnet-mode. These AIMD apparatus changes match a new clinical magnet mode application method. For most existing AIMDs, this can be accomplished through software upgrades or patches. For other AIMDs, hardware upgrades may be required.

In a first embodiment (FIG. 9), multiple placements of a clinical donut or equivalent magnet 210 over the AIMD magnetic field sensor (such as a Hall-effect, reed switch or a GMR sensor 200) (FIGS. 1H to 1K) including a deliberate time sequence are required to significantly reduce the chance of an inadvertent induction of magnet-mode. In a second embodiment (FIG. 10), multiple AIMD detected north-south or south-north flips of a magnet are required to induce magnet-mode. For the embodiments of FIG. 9 or 10 to reliably work in the clinical environment, clinicians must be taught the new universal clinical magnet placement sequence method shown in the flow chart illustrated FIG. 11

(this new clinical method is compatible with either multiple placements or multiple placements with magnet flips in between).

For example, it is highly unlikely that an iPhone 12 will be removed and replaced in a shirt pocket several times in a row, each time reversing the orientation of the magnet contained in the phone. On the other hand, clinicians can be trained, for example, to do a "triple-flip". With a triple-flip, the clinical magnet is placed with one side down and then, within a time period, such as 10 seconds, as one possible example, flipped over again, within seconds, flipped over again, and then lastly, flipped over a third time. The Hall-effect sensor 200 inside the medical device detects these flips from north to south or south to north and counts and time-sequence them such that it is only after the prescribed number of flips and interim time windows that the medical device enters into magnet-mode.

An alternative to this precise flip programming, is, if the clinician makes a mistake (misses the timing in one of the steps) and the AIMD does not enter magnet-mode at the last step, then the AIMD could be programmed to count an extra flip or even "x" extra flips to still enter magnet-mode (this few seconds of grace is an embodiment of the present invention, however, its implementation will be subject to discussions and determinations within the societies of the medical community).

Figure 9:
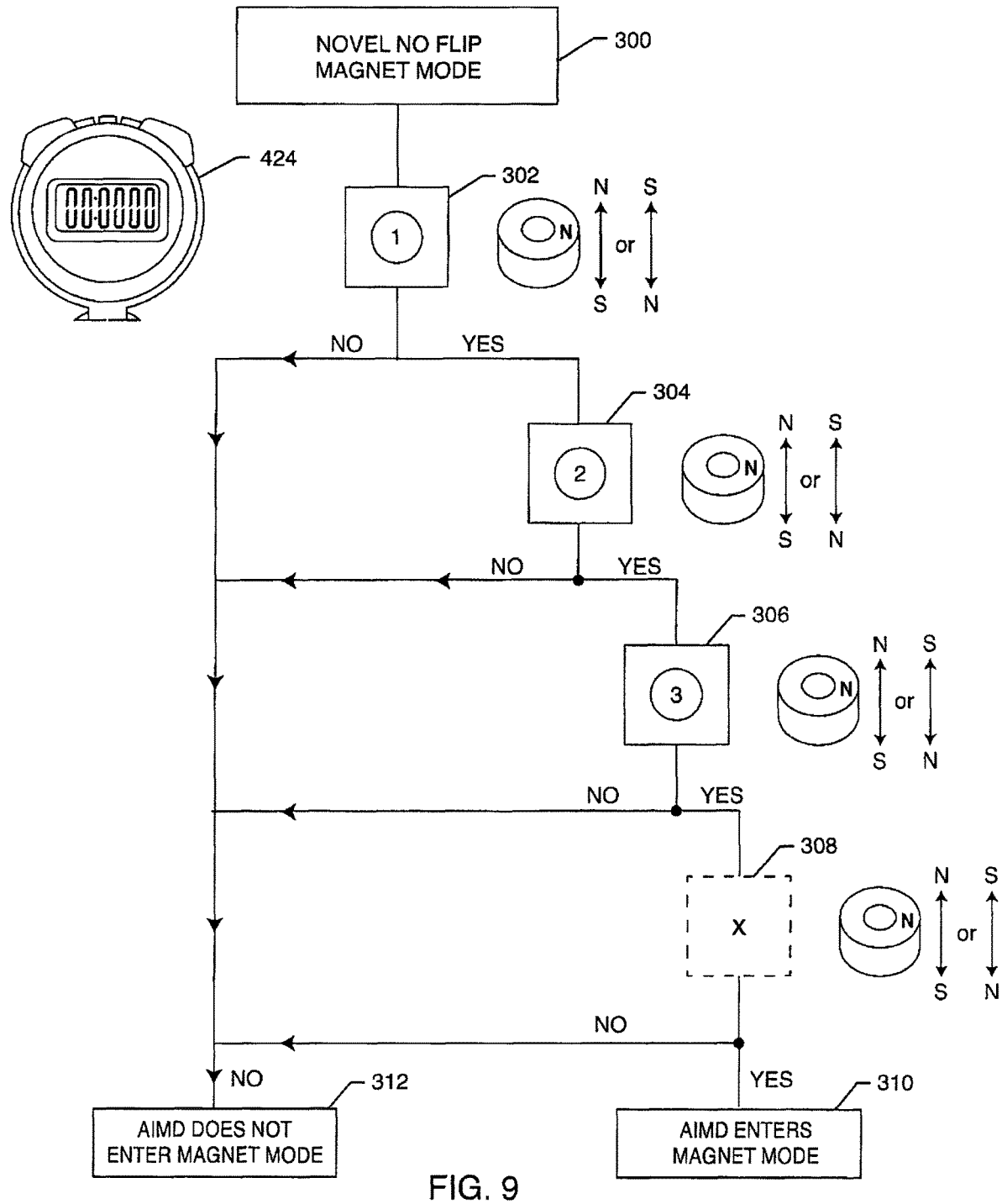
FIG. 9 is a flow chart of one embodiment of the present invention.
Figure 10:
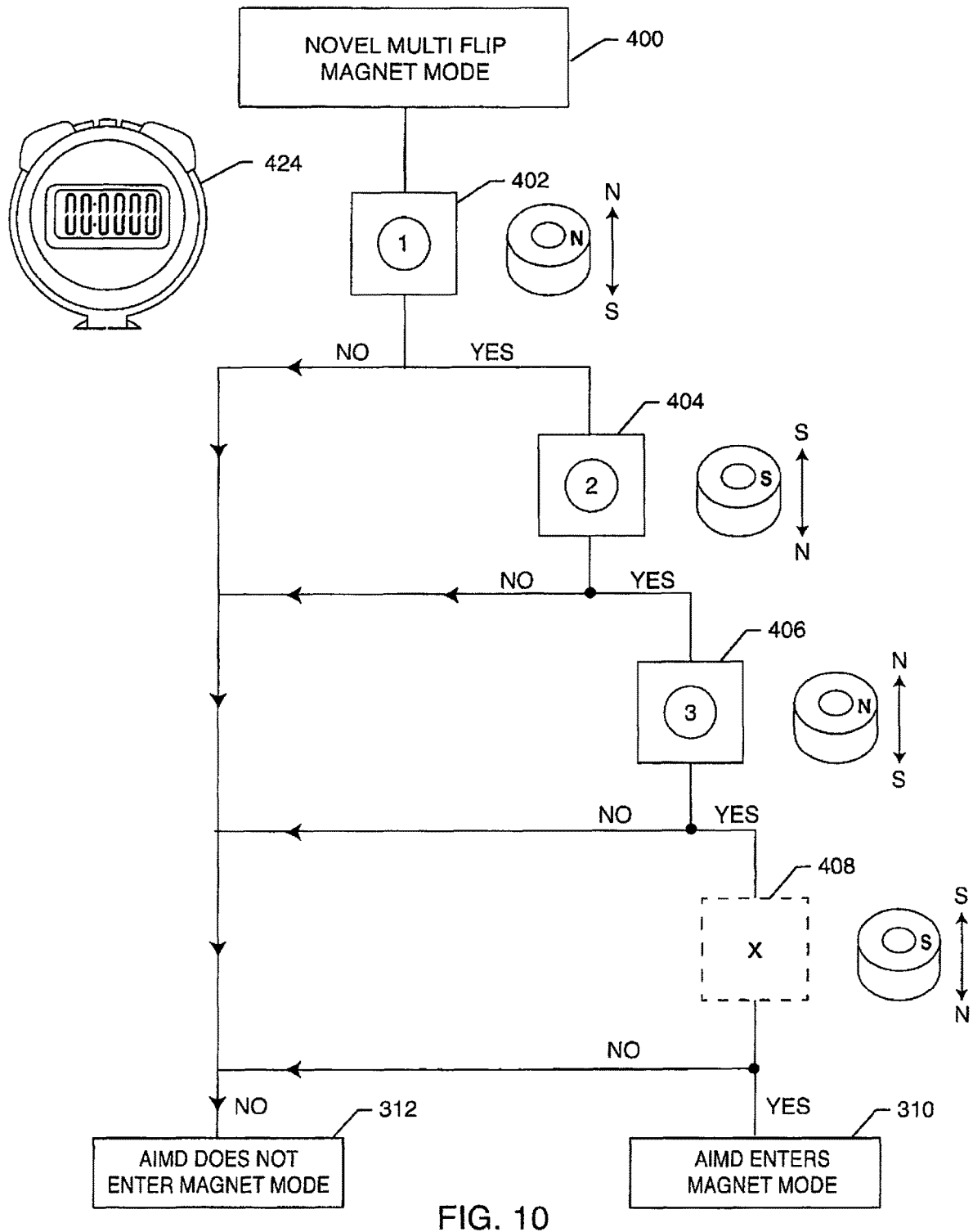
FIG. 10 is a flow chart of another embodiment of the present invention called the novel multi-flip magnet-mode 400.
Figure 11:
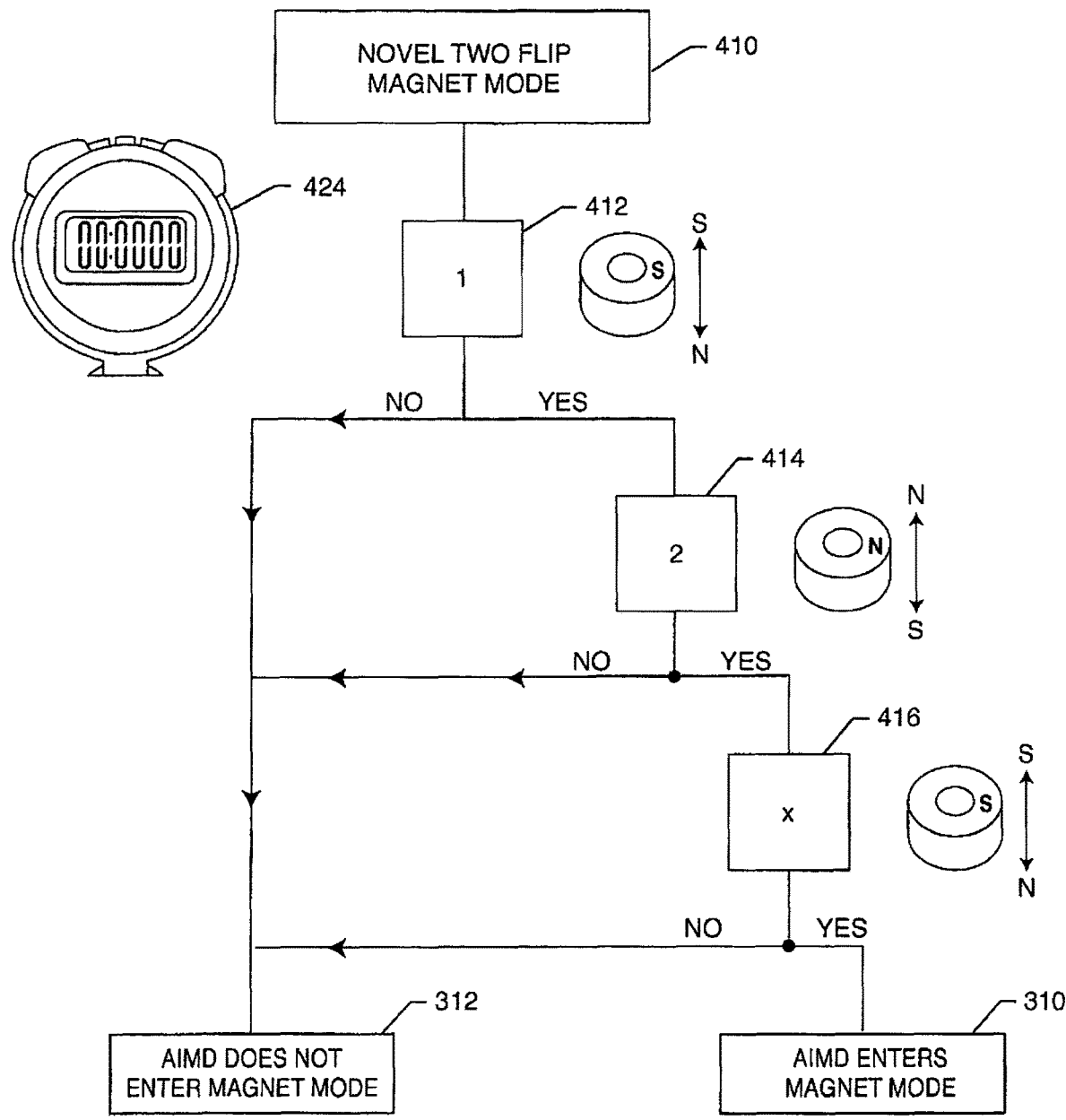
FIG. 11 is a flow chart 410 of a two-flip embodiment or a double-flip magnet-mode embodiment or an n-flip embodiment of the present invention.

FIGS. 9, 10 and 11 illustrate AIMD software or firmware logic and method flow charts of the present invention in which the number "x" (which can be any number from 2 to 100) is shown in the last logic step box 308, 408 or 416, respectively. The number "x" is defined herein as being the number of added steps after respective steps 306, 406 and 414 to the flow charts of FIGS. 9, 10 and 11. Illustrative examples of "x" will be given. It will also be appreciated that "x" can even be a negative number in some of the flow charts, meaning that a step is removed from the depicted sequence. In the present invention, there are always at least two placements and when a flip is being detected, at least one flip.

Also, with reference to FIGS. 9, 10 and 11, as defined herein, the letters $n_1$, $n_2$, $n_3$ and $n_4$ each represent a specified magnet minimum/maximum application or minimum/maximum magnet removal time period or window in seconds which can be any amount but in an embodiment varies generally from 1 second to 100 seconds. As defined herein, $n_2$ must always be greater than $n_1$, and $n_4$ must be greater than $n_3$, etc. When the subscript of "x" is an odd number (1, 3, 5 . . . ), then "x" is a minimum time placement in seconds. When the subscript of "x" is an even number (2, 4, 6 . . . ), then "x" is a maximum time number in seconds.

As a simple example using a single flip: there is a first magnet placement in close proximity to the AIMD of no less than $n_1$ seconds and no greater than $n_2$ seconds. Then, the magnet must be removed from being in close proximity to the AIMD within the $n_1$ to $n_2$ time window. Then, the magnet is flipped once or not flipped and placed back into close proximity to the AIMD in no less than $n_3$ seconds and no greater than $n_4$ seconds, which results in the AIMD entering magnet-mode.

FIG. 9 illustrates a flow chart of one embodiment of the present invention. This is known as the novel no flip magnet-mode 300. At a summary level, a clinical magnet is first placed in close proximity to the AIMD in step 302, the magnet is then removed from being in close proximity to the AIMD and then placed again in close proximity to the AIMD in second step 304. The magnet is then removed from being in close proximity to the AIMD and again placed in close proximity to the AIMD in the third step 306. When the number "x" in the last step 308 equals one (1) additional step, four magnet placements are performed before the AIMD enters into magnet-mode if and only if each placement and removal fall within a prescribed time sequence or window. If x=2, two additional placements and removals after step 306 are performed for a total of five placements of the magnet in close proximity to the AIMD. Thus, when x=1 in FIG. 9, there are four total placements. However, it will be appreciated that step 308 can be eliminated resulting in three magnet placements in close proximity to the AIMD, or both steps 308 and 306 can be eliminated resulting two magnet placements in close proximity to the AIMD before the AIMD enters into magnet-mode. If the goal is to keep an AIMD from inadvertently entering into magnet-mode, the preferred embodiment of the present invention is a minimum of four placements as illustrated when x=1 as illustrated in FIG. 9. In the present invention, "x" placements can be any number greater than or equal to 2. Referring to FIG. 10, which is the flip flow chart, it will be appreciated that the minimum number of flips is 1, meaning that the number of placements, in this case is two.

In step 302 of FIG. 9, the clinical magnet is first placed in close proximity to the AIMD. This activates the AIMD microprocessor programming logic which counts each placement, and when the logic totalizer reaches the specified number of correct placements within the correct time limits or time windows, it sends a signal or code within the AIMD circuitry to place the AIMD into magnet-mode. Operating in each step will be IF-THEN programming logic which will only produce a YES response in each step if the clinical magnet has been properly placed in no less than "$n_1$" seconds but no greater than "$n_2$" seconds. The IF-THEN logic counts the same or a different requirement for placement time and magnet removal and then placement time. In other words, magnet removal time and re-placement can be specified for no less than $n_1$ and $n_3$ seconds and no greater than $n_2$ and $n_4$ seconds. In an embodiment, for simplicity for the clinician to remember, $n_1$ seconds would equal $n_3$ seconds and $n_2$ seconds would equal $n_4$ seconds. For example, place the magnet over the AIMD implant each time for between 2 to 10 seconds, remove the magnet from being in close proximity to the AIMD, flip the magnet in no less than 2 seconds and no more than 10 seconds and then replace the magnet over the AIMD implant again.

There are many types of static magnet field sensors with a Hall-effect sensor, a reed switch and a GMR sensor being exemplary, but which do not limit the scope of the present invention. Stated simply, the programming logic of FIGS. 9 and 10 should be compatible with almost all types of magnetic field sensors that are sensitive enough to produce an output that can be used as an input to programming logic. Swiping or movement of the magnet 210 during these placements is contraindicated in the basic embodiments. Placing a dot or dots on the patient's skin with a marker pen would help the clinician to very accurately place the magnet 210 in the same location after each flip or placement. If the AIMD senses the magnet for a specified period of time along with a sufficient static magnetic detected field intensity, the microprocessor or equivalent logic circuitry of the AIMD produces a YES response, which leads to removal to a suitable distance and the next magnet placement 304 for a specified time.

For example, in step 302 of FIG. 9, the magnet must be applied and then removed from being in close proximity to the device to a distance of at least about 15 cm (about 6 in.), within a certain number of seconds, for example, 2 to 10 seconds. The preferred removal distance is about 15 cm (about 6 inches) which includes a wide margin for error. In all embodiments of the present invention, the magnet 210 removal distance is at least 1 cm from the skin surface over the AIMD implant location. Then, the magnet 210 must be reapplied within this same time window in step 304 of FIG. 9. If the magnet 210 is properly reapplied a second time in the specified time window, then in step 304, a YES response is created, which leads to step 306. Again, within the same time window (such as 2 seconds minimum to 10 seconds maximum), the magnet 210 is again removed and then reapplied a third time in close proximity to the device. Each magnet application and removal sequence is defined herein as one magnet iteration. This produces a YES response in step 306 in FIG. 9. Step 308 in FIG. 9 shows that any number "x" of removals and reapplications (iterations) can be specified and programmed into the AIMD's computer logic.

In box 308, "x" can even be a negative number, such as −2, with two boxes 306 and 308 being eliminated or subtracted from the magnet placement and removal sequence. In that case, the total number of placements is 2, namely two magnet placements indicated by boxes 302 and 304 with an interim removal. This is the most fundamental aspect of the present invention in order for an AIMD to enter into magnet-mode in step 310. In that respect, step 304 is the final magnet placement step when x=−2.

Regardless the value of "x" in the last step, upon performing the last magnet placement, the AIMD remains in magnet mode for as long as the magnet is in close proximity to the AIMD (for example, taped in place). So, in all embodiments, whether they be placements or flips, the last step does not embody a minimum and maximum time window for a removal, as a removal can be from seconds to hours or even days. The AIMD will stay in magnet-mode for as long as the magnet 210 remains in close proximity to the implanted AIMD magnet field sensor. The magnet 210 can be taped down, for example, during surgery, to suspend therapy. If any of these timing sequences and placements are not done correctly (for example, the clinician drops the magnet), this results in a NO response, and the AIMD does not enter magnet-mode in step 310 in FIGS. 9, 10 and 11. After a predetermined time-out period (for example, ten seconds), the clinician can start again from the top of the FIGS. 9, 10 and 11 flow chart and repeat the sequence.

Referring once again to FIG. 9, a timer or a clock 424 is indicated. However, the clock is not generally necessary, for example, for an approximate timed magnet application and removal sequence (for example, as 3 seconds). All a clinician has to do is remember the number of placements and possible flips and count or sing a line from a tune between each removal and replacement of the clinical magnet. There is a tradeoff between the time precision of placement and removal and a greater immunity against inadvertent entry into magnet-mode caused by a portable device or toy with a strong magnet. For example, a requirement for magnet placement of 5 seconds, plus or minus 1 second, followed by a removal of 3 seconds, plus or minus 1 second, would be more difficult, requiring the clinician to watch something like a digital timer. Such a tightly controlled time sequence would have high immunity to inadvertent magnet-mode entry but is more difficult to implement in practice (particularly in an emergency where rapid magnet placement is required).

The inventors expect that the international Heart Rhythm Society (HRS) in conjunction with the international neurostimulator society (NANS) will work together to determine suitable time sequences. HRS has requested prototypes for testing to assess the human factors and ease of performing the sequences. Ultimately, it will be the responsibility of the ISO 14708-1 working group to standardize a universal clinical magnet timing sequence for all AIMDs. Each AIMD type can have a different sequence, for example, life sustaining CIED or AIMD devices like pacemakers and ICDs might require four or five magnet placements. But, for a spinal cord pain stimulator (which prevents pain but is not life sustaining), two total placements might suffice. Deep brain implants can be considered life sustaining when the patient is driving a car and the like as inadvertent magnet-mode entry could suspend device therapy resulting in erratic and uncontrolled movements.

In an optional embodiment, the steps of FIG. 9 can have the added requirement that the static field reed switch or Hall-effect sensor 200 does not produce a YES response unless a predetermined static magnetic field strength is also achieved during each placement of the clinical magnet. This requires repeated accurate spatial positioning in each magnet placements. AIMD implant depth, patient body mass index and skin thickness (related to age) are important variables. This is why clinical magnets are usually much stronger than 9 Gauss.

Providing a skin locating dot or even a permanent tattoo dot or mark as described herein would greatly assist positional accuracy. Such accurate positional placement enables yet another alternative embodiment wherein the sensed magnetic field intensity of each magnet placement can have an upper and lower limit. This would additionally limit AIMD inadvertent entry into magnet-mode, for example, from an iPhone moving/sliding/swiping around in a shirt pocket.

In any of the embodiments of the present invention, the ISO 14117 10 Gauss (1 mT) limit could also be significantly raised, for example, to 500 Gauss or even higher. However, this is not an embodiment of the present invention as this requires that most clinical magnets 210 around the world be replaced with much more powerful magnets. In combination with this, AIMD Hall-effect sensors 200 would need to be re-programmed such that they do not trigger below these new higher ISO 14117 levels. Powerful magnets of 500 Gauss or higher will make it less likely that a portable magnet in a device or toy can inadvertently induce AIMD magnet-mode, however, such powerful magnets become very impractical in many ways in that they will attract other objects and even be quite difficult to pry off of a filing cabinet, and the like. There is no U.S. agency that regulates the strength of a static magnet that a portable device or toy may incorporate, so the idea that nothing more powerful than 500 Gauss will show up is also flawed (reference the Nikken 1 Power chip Medallion Charm manufactured by Kenco which may be attached to a lanyard worn around the neck or placed over any body area). As previously stated, the Nikken 1 advertises a magnetic field strength of 900-1000 Gauss.

In the present invention, and as described in FIGS. 10 and 11, when the magnet 210 is removed or flipped, it must be removed at a suitable distance from the AIMD such that the magnetic field sensor, for example the Hall-effect sensor 200, cannot trigger. A very conservative distance for this purpose is about 15 centimeters (about 6 inches), but it could be closer. In the present invention, removal and flipping the magnet 210 is described as any distance from about 1 to about 30 centimeters or greater, with about 15 cm being the preferred distance.

FIG. 10 is a flow chart of another embodiment of the present invention called the novel multi-flip magnet-mode 400. This is different than the magnet-mode described in FIG. 9, where it was not necessary to flip the magnet 210 between placements. Clinical magnets are generally not marked with north or south on their faces (so clinicians do not know which face of the magnet is north or south).

To enable the multi-flip magnet-mode 400 of FIG. 10, the AIMD Hall-effect sensor 200 would first be programmed to detect magnetic field polarity as well as intensity (a reed switch cannot detect polarity). Moving down the flow chart, in the first placement in step 402, a donut magnet 210 is placed over the AIMD. It does not matter in this first step whether the magnet 210 is placed on the patient's skin over the AIMD in either a north or a south polarity. The Hall-effect sensor 200 and its associated programming circuits will simply detect that a magnet of suitable strength appeared and note that the magnet was of a particular polarity, for example, a north polarity. Importantly, in the second step 404, after the magnet 210 is properly removed within the time sequence or time window of 402, the clinician flips the magnet 210 over and places it again over the AIMD. This reverses the magnetic field polarity, for example, from north to south or south to north. A YES response in the second step 404 means that within a specified time interval, for example, 5 seconds, the magnet 210 was removed, flipped over and then placed down again over the AIMD in a third placement step 406. The clinical magnet is then removed, flipped and placed again in a fourth placement step, as shown in block 408. And, if this sequence is done within the correct minimum and maximum time windows, a YES response is elicited and the AIMD enters magnet-mode. In this case, with the added number of steps x=1, then step 408 becomes the final step and the AIMD remains in magnet-mode for as long as the clinical magnet is in close proximity over the implant. It is appreciated that any number of "x" additional flips and placements can be specified in box 408.

In an embodiment related to the flow chart shown in FIG. 10, x can be −1, meaning that step 406 is removed from the sequence. However, the least number of flips allowed in the present invention is 1 between a first and a second placement of the clinical magnet over an AIMD. For "The Triple Flip" embodiment of the present invention, x in box 408 is equal to +1, indicating one more removal, flip and placements after step 406.

For example, a placement 402 followed by a triple flip would be easy to remember, wherein one places the magnet over the AIMD and then within 10 seconds, flips it over, and then within 5 seconds, flips it over again and then within 5 seconds, places the magnet back over the AIMD after the third flip (the 5 second window or period is just an example, which can be changed to any specified time sequence). In general, the application times and removal and flip and reapplication durations all have minimum and maximum limits. These time limits or time windows are important to prevent a portable device, such as a portable electronic device, like the iPhone 12, from being inadvertently flipped to trigger magnet-mode. It becomes highly unlikely either for FIG. 9 (the placement method) or FIG. 10 (the placement plus flip method) that the specific time windows would happen inadvertently using an iPhone, and the like.

In any of the embodiments of the present application, one could change the time duration or time sequence from one magnet application to another, for example, 3 seconds, 5 seconds, 10 seconds, etc., to cause the AIMD to enter its magnet-mode 310.

Referring once again to FIG. 10, "The Triple Flip" version of the multi-flip flow chart occurs when (x) in step 408 equals 1 additional step after step 406 (step 408 then becomes the third and final flip). This means that in step 408, there is no time window in which the magnet must be removed. As long as the magnet is held in close proximity to the AIMD, the AIMD stays in magnet-mode.

Some AIMD manufacturers may want to put a maximum time limit on magnet-mode. For example, they may want to terminate magnet-mode after one hour to prevent too long a period of asynchronous pacing. That is part of magnet-mode and not part of the present invention. So, the magnet-mode itself, and what therapy or lack of therapy the device delivers during magnet-mode is outside the scope of the present invention, including how long the device stays in magnet-mode before it times-out. Most AIMDs that the inventors are aware of will likely not have a maximum time limit and instead, will stay in magnet-mode for as long as the magnet is placed properly over the AIMD.

Still referring to FIG. 10, for "The Triple Flip" embodiment, the clinical magnet 210 is first placed on the patient's skin over the AIMD with any polarity in step 402 (the AIMD circuit logic records a first YES response), then, for example, within two to ten seconds (an example of a tolerance), the magnet is removed and flipped over within a specified time tolerance (the $1^{st}$ flip is recorded by the AIMD's logic)), and then placed near or adjacent to the patient's skin over the AIMD a second time for a specified time tolerance or time window "n" in step 404 (the AIMD circuit logic records a second YES response), then the magnet is removed and flipped over within a specified time tolerance or time window (the $2^{nd}$ flip) and again placed over the AIMD in step 406 (the AIMD circuit logic records a third YES response), and then within another time tolerance or time window, the magnet 210 is removed and flipped over again (the $3^{rd}$ and final flip) in step 408 (and the AIMD logic circuits detect and record a fourth YES response). In completing step 408 (three flips) properly according to the above sequence and time tolerances (without any NO responses), the AIMD enters its magnet-mode in step 310. The AIMD will stay in magnet-mode for as long as the clinical magnet is kept/held in place over the AIMD (for example, taped down over the AIMD implant).

If any of these steps are done incorrectly or not within the proper time sequence or time window, a NO response means that the AIMD does not enter magnet-mode (step 312).

"The Triple Flip" described above is one preferred embodiment of the present invention because:

1. It has a sufficient number of flips so that inadvertently flipping an exemplary iPhone or a child's toy in the same manner and timing become highly unlikely.

2. The term "Triple Flip" is catchy and easy for clinicians to remember.

3. Co-inventor Robert Stevenson's wife Wendy was the U.S. National Gymnastics champion in 1976 and slated to be a member of the U.S. Olympics Team (she was injured just before the competition). Her specialty was floor exercises and, in particular, "The Triple Flip."

Again, the objective of the present invention is to make it highly unlikely that a powerful magnet in a portable device, such as the iPhone 12 or iPhone 13 would be flipped over in such a sequence that the ring magnet 232 in the phone causes the AIMD to inadvertently or inappropriately enter magnet-mode.

FIG. 11 describes a universal AIMD clinical magnet placement method. The reason this is called a universal method is that it captures the novel no flip magnet-mode depicted in FIG. 9 and also the novel multi-flip magnet-mode depicted in FIG. 10.

Referring to FIG. 11, it is not important that the clinician know which side of the magnet is north or south or how the AIMD is programmed. In the first magnet placement in step 412, the clinician simply places the magnet on or adjacent to the skin (for example, over a bandage) over the AIMD implant. During the placement 412, there is a specified time period or window with a minimum and maximum time that the clinical magnet must be placed in close proximity over the AIMD device. Then, in the second step 414 and within a specific minimum and maximum time sequence or time window, the clinical magnet is removed to a suitable distance so that the AIMD no longer detects the magnet, for example, to about 15 cm, the magnet is flipped and then placed back down in its original position over the AIMD implant. This constitutes the first flip. In the third step 416, since placement of the magnet in step 414 occurs within the proper minimum and maximum time window, the AIMD enters magnet-mode. In this example, "x" in box 416 is equal to zero, meaning there isn't an additional placement of the magnet over the AIMD after step 414. However, when x=1, there is one additional step of removing, flipping and placing again, within a minimum and maximum time window after step 414, and this then becomes "The Triple Flip".

Still referring to FIG. 11, flips have been descried as part of a universal magnet mode. However, the AIMD may or may not be detecting these flips. This all depends on the type of static magnetic field sensor that the AIMD has. For example, if the AIMD has a reed switch, the placements would be counted and totaled before the AIMD enters into magnet-mode. For some AIMDs, for example, those with a programmed Hall-effect sensor, placements and flips of the clinical magnet are both counted, which gives a higher level of security against inadvertent magnet-mode entry. It is not important that the clinician know whether the AIMD is counting the flips, or not. However, it is important that the clinician apply and flip the magnet as described in flow chart FIG. 11 so that both cases are covered.

Referring back to FIG. 9, where the AIMD is not programmed to sense north and south placements, the AIMD, which may have a reed switch, counts the number of placements within the prescribed time periods and if every step of the sequence is done correctly, there is a YES response and in step 310, the AIMD enters magnet-mode. Referring once again to FIG. 11, for an AIMD, for example, with a Hall-effect sensor that is reprogrammed to sense and count polarity reversals, each flip and placement of clinical magnet over the implanted AIMD is counted/recorded by the software, and when "n"=1 in step 416, "The Triple Flip" has been performed, which elicits a YES response, thereby placing the AIMD into magnet-mode in step 310.

According to the present invention, it is believed that the triple placements (FIG. 10) or "The Triple Flip" (FIG. 11) sequence of steps is sufficient to prevent inadvertent activation from magnets contained in portable electronic devices or even in children's toys, and like. FIGS. 10 and 11 describe programming and even hardware design changes to AIMDs. The logic diagrams of FIGS. 10 and 11 are part of AIMD new hardware sensing and new/revised AIMD software logic where each YES or NO response is part of an If-Then type of software control flow response. In computer science, conditionals (that is, conditional statements, conditional expressions and conditional constructs) are programming language commands for handling decisions. Specifically, conditionals perform different computations or actions depending on whether a programmer-defined Boolean condition evaluates to true (YES) or false (NO). In terms of control flow, the decision is always achieved by selectively altering the control flow based on some condition (apart from the case of branch predication). In the present invention, magnet-mode is entered only after the number of prescribed YES responses occur within the specified time windows. It will be up to various medical societies, including Heart Rhythm Society and perhaps NANS, and even ISO to decide just how many placements/flips and the timing sequences that will be appropriate.

Figure 12:
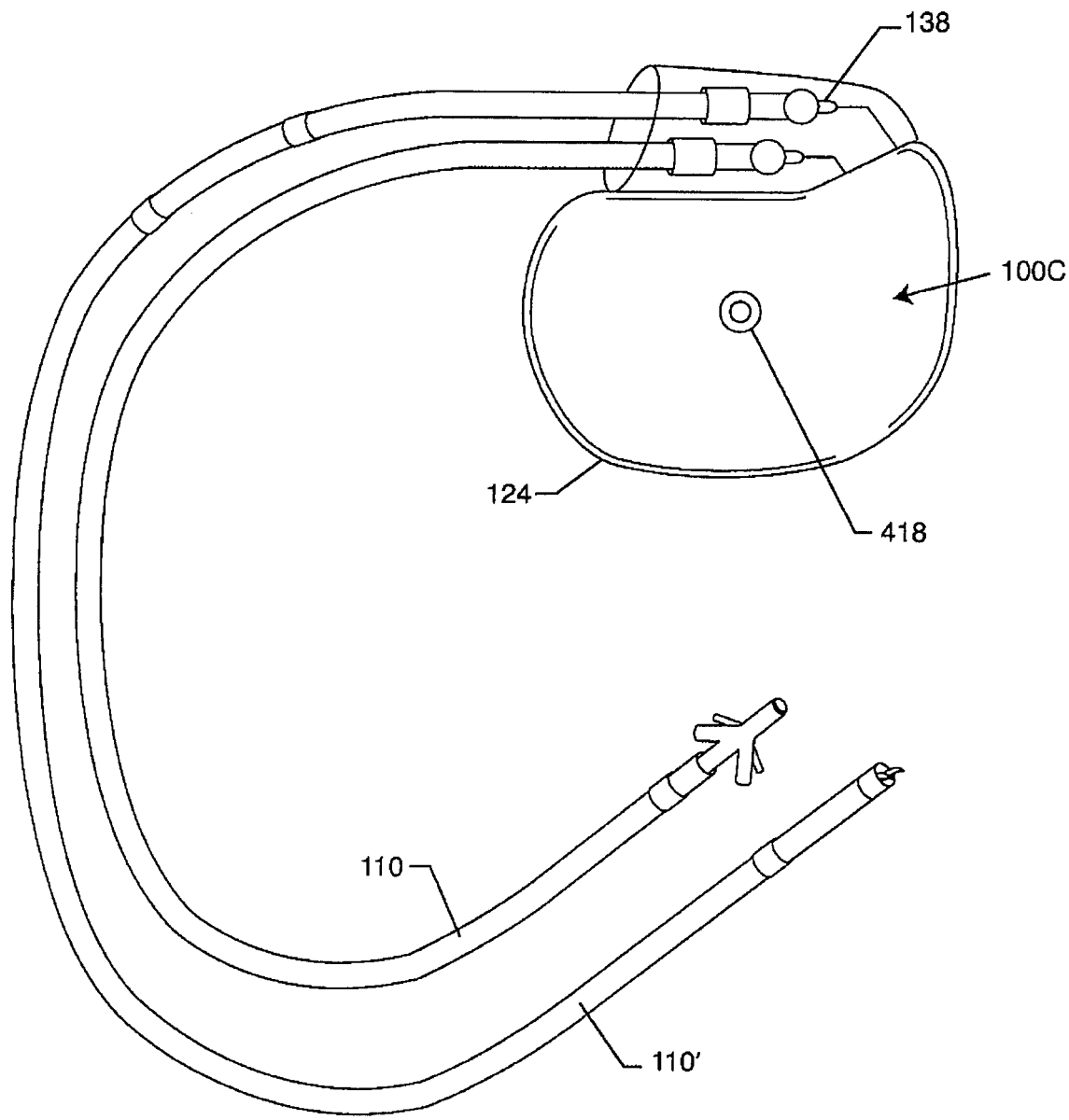
FIG. 12 is a schematic view of a prior art cardiac pacemaker 100C having a laser engraved skin target 418 for alignment of a magnet to place the pacemaker in magnet-mode.

FIG. 12 is a schematic view of a cardiac pacemaker 100C, as previously depicted in FIG. 1. The pacemaker 100C has a header block 138 into which cardiac leads 110 and 110' are plugged. There is a laser engraved target 418 which can be a circle within a circle or a circle with cross hairs or any other ISO adopted symbol. The purpose of this laser engraved marking on the outside of the pacemaker housing is to show the implanting physician exactly where the reed switch or Hall-effect sensor 200 (or equivalent) is located inside the hermetically sealed AIMD housing 124. The AIMD magnetic field sensor 200 typically is located on a circuit board 130 (FIG. 1D) and may not be centered in the AIMD housing as shown in FIG. 12 (it is often off to the side). By knowing the magnetic field sensor location, the implanting physician during surgically building or closing the AIMD implant pocket can now affix a tattoo or permanent ink dot or mark on the patient's skin directly over the magnet field sensor 200. Such a mark or dot helps to enable the present invention where repeated placements or flips of a toroidal clinical magnet is required for the AIMD to properly enter magnet-mode.

Figure 13:
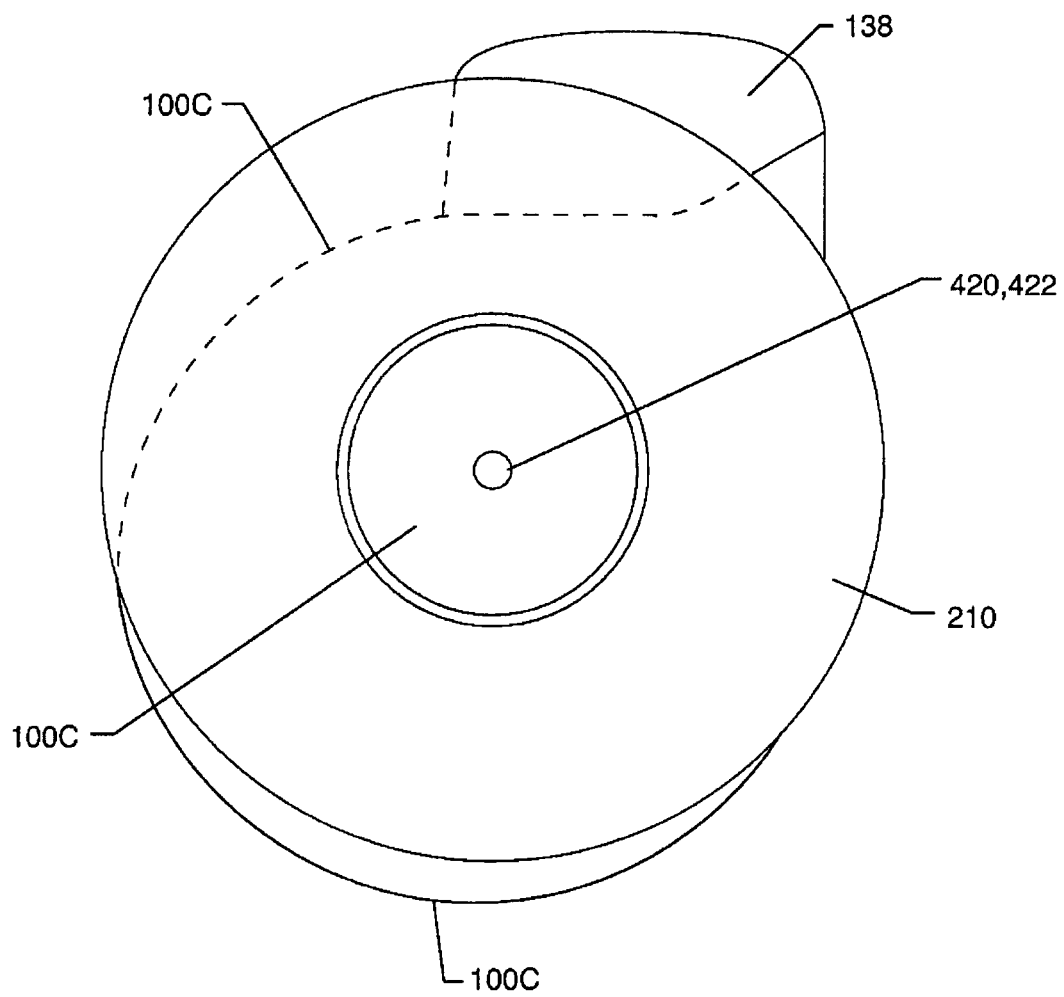
FIG. 13 shows the pacemaker 100C of FIG. 12 with a donut magnet 210 aligned with a dot 420 on the skin 422 of a patient to induce magnet-mode for the pacemaker.

FIG. 13 shows the pacemaker 100C of FIG. 12 implanted in the human body. Spatially located over the pacemaker 100C is a typical donut-shaped magnet 210, which is intended to induce magnet-mode. A permanent dot 420 or a temporary (surgical pen) mark 422 is shown on the skin of the patient. This is to facilitate the present invention such that with each removal and reapplication of the magnet 210 of the AIMD, or in other embodiments, each flip of the magnet, the magnet is centered over the AIMD at approximately the same location. This aspect of the present invention, therefore, prevents inadvertent swiping of the magnet. The skin mark 420, 422 can be a small tattoo dot or permanent ink dot that is applied at the time of implantation and spatially aligned with the target 418 that was laser engraved on the pacemaker housing 124. The clinician can also take a surgical marking pen or even a sharpie and place a dot on the patient's skin after palpitating and feeling the outline of the pacemaker 100C. In the case where the magnet 210 is not donut-shaped or has a solid core, it is appreciated that two or three markings around its outside circumference or perimeter can be applied to the patient's skin either permanently or temporarily. The features illustrated in FIGS. 12 and 13 are optional embodiments of the present invention.

Figure 14:
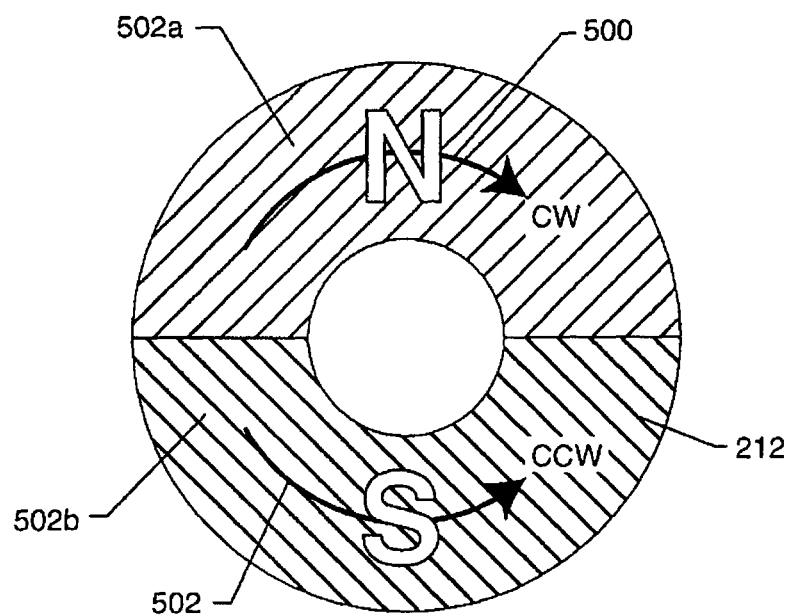
FIG. 14 is a schematic view showing that precise clockwise and then counterclockwise rotation of a ring magnet 212 that can be used to safely induce magnet-mode in an AIMD according to the present invention.

FIG. 14 illustrates that precise clockwise and then counterclockwise rotation of a ring magnet 212 could also be used to safely induce magnet-mode. A disk/toroidal or cylindrical magnet 212 can be magnetized in the axial direction (i.e., one flat side is north, the other flat side is south) or diametrically (i.e., one half of the curved side is north, the other curved side is south.) Therefore while FIGS. 10 and 11 demonstrate a series of polarity inversions introduced by flipping the magnet side touching or near the patient's skin, the polarity inversion technique can also be sensed by a three-axis Hall-effect sensor 200 by rotating the magnet 212, for example, in 90° to 180° increments. In that manner, each incremental rotation achieves the same relative polarity inversion accomplished by a magnet flip.

Figure 15:
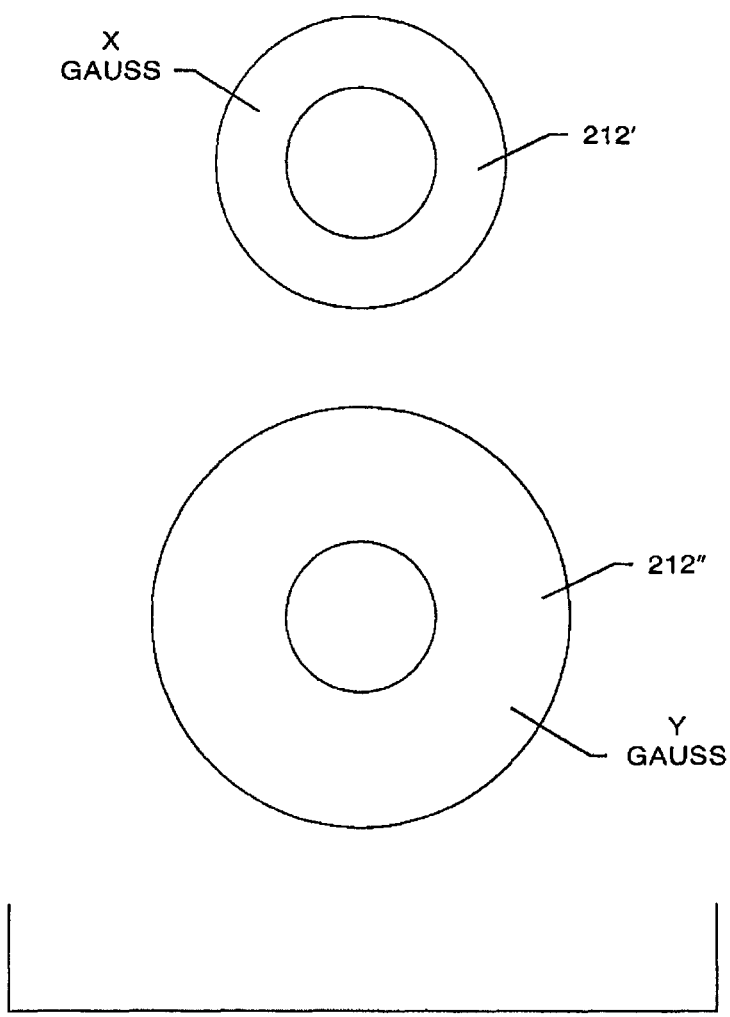
FIG. 15 is a schematic illustrating that magnet-mode in an AIMD can be safely induced by first applying a lower strength magnet 212' and then within a specific time period, applying a higher strength magnet 212".

Referring once again to FIG. 14, the toroidal or donut ring magnet 212 has been separated into a north half 502*a* and a south half 502*b*. This is different than the previously described conventional ring- or donut-shaped magnet 210 that has north on the top and south on the bottom. By turning magnet 212 fully (or partially) clockwise and then fully (or partially) counterclockwise and then fully clockwise again, the Hall-effect sensor 200 can be programmed to sense alternating south and north fields. However, this technique requires replacing all clinical magnets throughout the world with the illustrated bifurcated magnet 212, but is, nonetheless, a safe and effective way of having an AIMD entering magnet-mode. This technique also makes it highly unlikely that a magnetic emitter, such as an iPhone 12 in a shirt pocket, will inadvertently or inappropriately cause an AIMD to enter into magnet-mode. In summary, FIG. 14 represents an alternative embodiment of the present invention. FIG. 15 is a schematic illustrating that magnet-mode in an AIMD can be safely induced by first applying a lower strength magnet 212' and then within a specific time period, applying a higher strength magnet 212". Again, any number of sequences, including "n" sequences, of a weaker and stronger magnet could be used to assure that inadvertent movement of an iPhone 12 in a shirt pocket, and the like, will not induce magnet-mode in an AIMD. Referring once again to FIG. 15, this drawing shows that the smaller donut-shaped magnet 212' uses a static magnetic field strength of X Gauss and the larger, more powerful magnet 212" produces a static magnetic field strength of Y Gauss. In one embodiment, the clinical magnet has a strength that is between about 80 Gauss and 200 Gauss. It is appreciated that the magnets 212' and 212" of FIG. 15 can be the same size and shape. However, providing them of different sizes helps the clinician ascertain which of the two magnets has a stronger magnetic field than the other.

Figure 16:
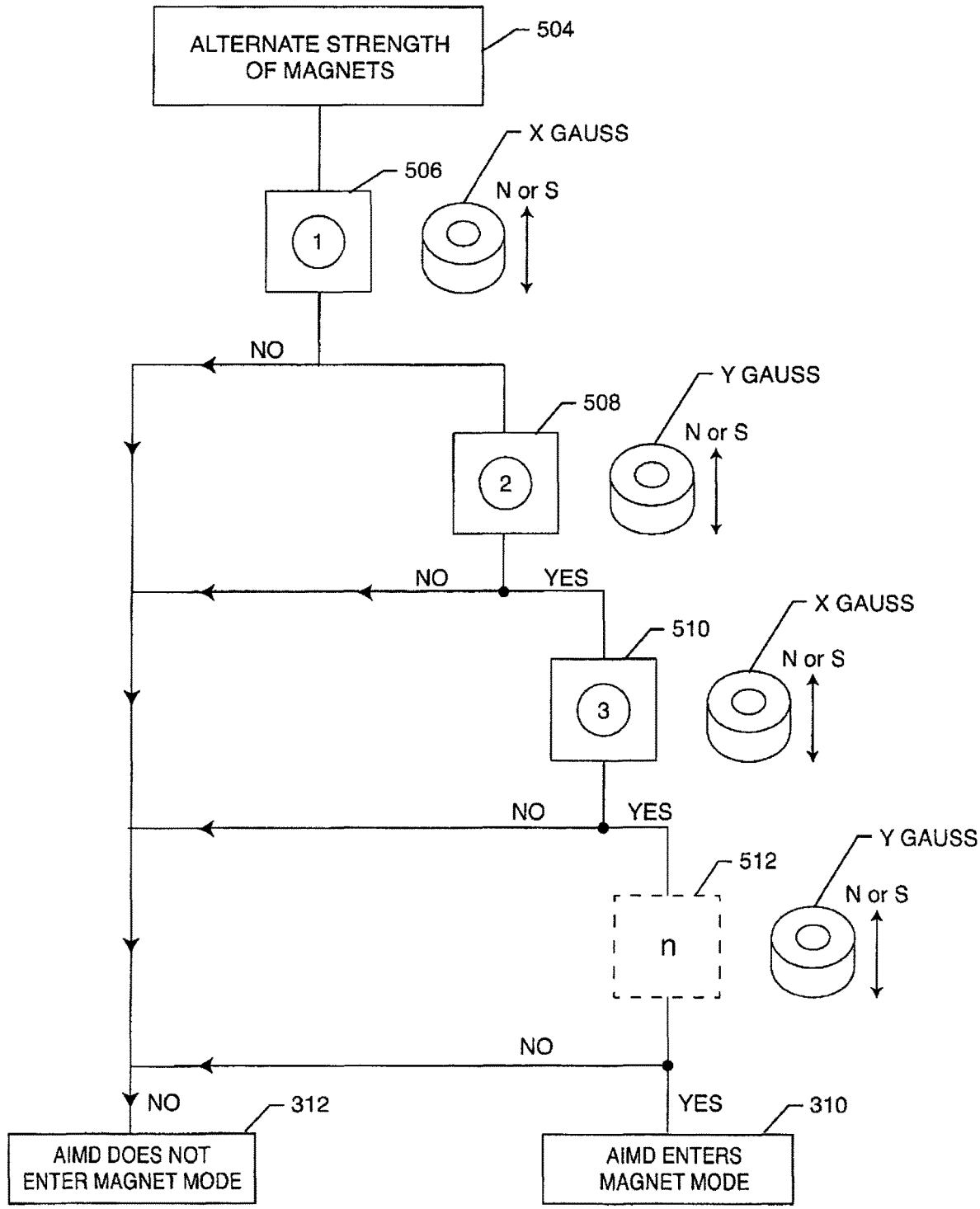
FIG. 16 is a flow chart 504 showing a typical application and timing sequence of alternate strength magnets to an AIMD as described in FIG. 15.

FIG. 16 shows a block diagram 504 of a typical application and timing sequence of alternate strength magnets 212' and 212" shown in FIG. 15. In first step 506, the X Gauss 212' magnet is placed over the AIMD and then within a specific time interval or time window, it is removed at a suitable distance (for example, more than 6 inches). Then, a different magnet of Y Gauss 212" is repositioned over the AIMD in a second step 508. Then again, within a specific time sequence or time window, the Y Gauss magnet 212" is removed, and the lower strength X Gauss magnet 212' is applied over the AIMD in step 510. As before, the YES response in the third step 510 can be repeated any number of "n" additional times 512 (where "n" is greater than 1 and less than 100). If all of these steps are done correctly, the AIMD will enter its designed magnet-mode in step 310. Of course, this process requires the use of two different strength magnets 212' and 212" that must be properly labeled and distributed worldwide.

Figure 17:
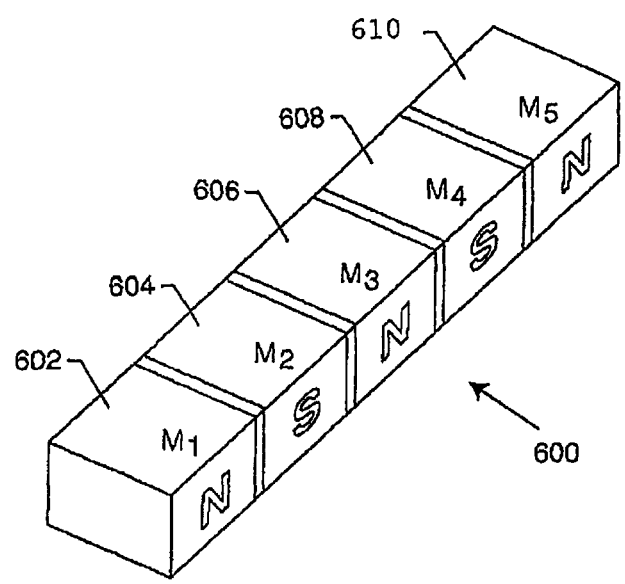
FIG. 17 is a perspective view of a strip magnet with various magnets $M_1$ through $M_5$ that alternate from north to south to north.

FIG. 17 illustrates a strip magnet 600 with various magnets $M_1$ through $M_5$ that alternate from north to south to north. The strip magnet 600 can have any number of magnetic sections 602, 604, 606, 608 and 610 and is similar to a magnetic door lock. In this embodiment, the bar magnet 600 is swiped over the AIMD, which causes the Hall-effect sensor 200 to detect within the swipe period the number of polarity reversals and whether those polarity reversals are in the programmed sequence needed to cause the AIMD to enter magnet-mode. It is appreciated that any magnetic sequence with the bar magnet 600 can be programmed into the AIMD's logic, for example, north-north-south-south. Bar magnet 600 can have any number of north or south segments generally between 2 and 20. Again, the bar magnet 600 of FIG. 17 requires replacing all of the clinical donut-shaped magnets in use throughout the world. Additional embodiments using the bar magnet 600 can include partial rotations as represented in FIG. 16, but not full polarity inversions.

Figure 18:
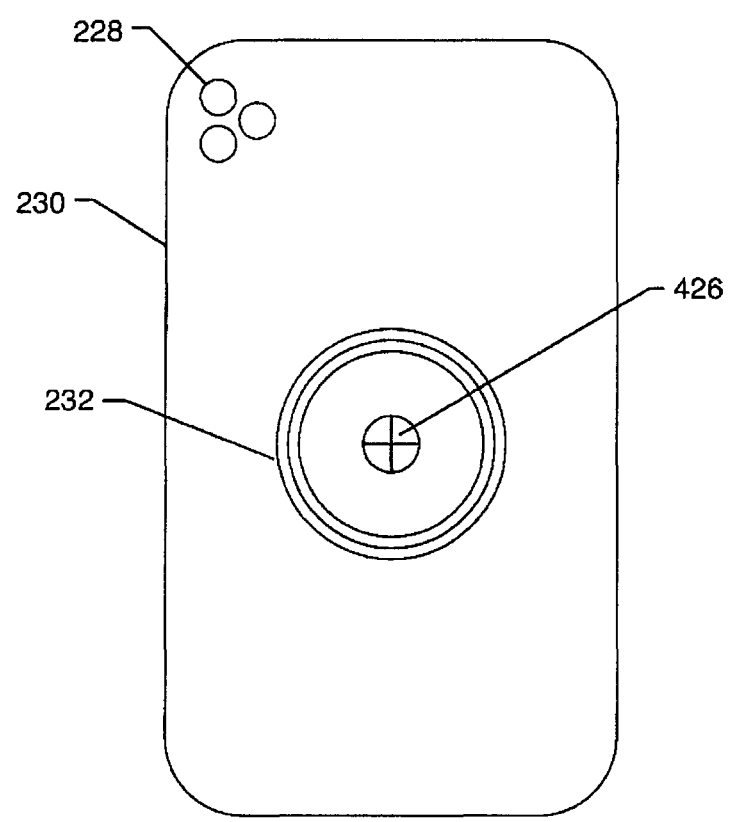
FIG. 18 illustrates a modification to an iPhone 12 (or any other portable electronic device that has a strong magnet) with the addition of a target 426.

FIG. 18 Illustrates a modification of the iPhone 12 (or any other portable electronic device that has a strong magnet) with the addition of a target 426. As shown, this could be a painted-on circle or imprinted circle with cross hairs, or any other target that is part of an ISO Standard. This modification is intended to change an iPhone 12 so that it can be used in an emergency as a deliberately applied clinical magnet. For example, referring once again to FIG. 9, instead of using the donut-shaped magnet 210, the iPhone 12 can replace the magnet 210 and be used as described for the no flip magnet-mode 300 technique for placing an AIMD in magnet-mode. In other words, ring magnets such as those in the iPhone 12, with a proper timing sequence, can be used by a patient or even a clinician to deliberately induce magnet-mode. This can result in the iPhone 12, and the like, being taped down over the implant in an emergency to keep magnet-mode properly induced. In that respect, the iPhone 12, iPhone 13, Apple watch and similar portable electronic devices with a strong magnet can be used with the no flip technique illustrated in FIG. 9, or the multi-flip techniques of FIGS. 10 and 11.

Referring back to FIGS. 9, 10 and 11, in another embodiment a form of magnet placement code can be programmed into the AIMD software (for example, Morse code). In this case, a particular AIMD such as a cardiac pacemaker may have multiple magnet-modes. To enter each particular mode, the placements and flips are varied. For example, for AIMD magnet-mode one- or two-timed placements of FIG. 9 also require a flip as illustrated in FIG. 10. To have the AIMD enter an alternate magnet-mode, there might be one placement in accordance with FIG. 9, and then two or more flips in accordance with FIG. 10. The number of combinations and permutations are large. This Morse code embodiment is not possible with reed switches or GMR, or other non-polarity sensing AIMDs.

In summary, the present invention changes the magnet-mode of an active implantable medical device (AIMD) such that repeated application of a clinical magnet in a predetermined and deliberate time sequence will induce the AIMD to enter into its designed magnet-mode. In that manner, the present invention is directed towards prevention of inadvertent entry of an AIMD into magnet-mode caused by the static magnetic field associated with the magnet in a portable electronic device, children's toy, and the like. It is very important that life-saving implantable medical devices do not enter magnet-mode unless it is done deliberately. Magnet-mode is intended as a design feature in an AIMD for a short period of time when a physician interrogates the device, performs a surgical procedure, and the like. Magnet-mode was never intended for prolonged use, such as could inadvertently happen when the magnet in a portable hand-held device is placed in relatively close proximity to the implanted device. In one embodiment of the invention, the clinical magnet is applied close to and over the AIMD and removed a specified number of times within a specified timing sequence. In another embodiment of the invention, the clinical magnet is applied close to and over the AIMD and flipped a specified number of times within a specified timing sequence. This makes it highly unlikely that the magnet in a portable electronic device, children's toy, and the like can inadvertently and dangerously induce AIMD magnet-mode.

Although several particular embodiments of the present invention have been described in detail for purposes of illustration, various modifications may be made without departing from the scope of the invention. Accordingly, the present invention is not to be limited, except by the appended claims.

What is claimed is:

1. An active implantable medical device (AIMD) system, comprising:
   a) an AIMD that is configured to deliver electrical stimulation therapy to body tissue and/or sense electrical biological signals from body tissue, wherein the AIMD comprises a housing containing a magnetic field-detection sensor connected to electronic circuits;
   b) a static strip magnet comprising:
      i) a first static magnet of at least a first defined Gauss and of a north or south polarity;
      ii) a second static magnet connected to the first static magnet, wherein the second static magnet is of at least a second defined Gauss and of a north or south polarity that is opposite the polarity of the first static magnet; and
      iii) a third static magnet connected to the second static magnet, wherein the third static magnet is of at least a third defined Gauss and of a north or south polarity that is the same polarity as that of the first static magnet,
   c) wherein the electronic circuits of the AIMD have been programmed to register when the static strip magnet has been swiped across the AIMD so that when the magnetic field-detection sensor detects a defined north and south polarity sequence of the first, second and third magnets, the electronic circuits have been programmed to enter into magnet-mode with electrical stimulation therapy of the body tissue and/or electrical sensing of biological signals from the body tissue being suspended, maintained in a preset mode, and/or placed in a programmed mode.

2. The AIMD system of claim 1, wherein, upon commencement of magnet-mode, the electronic circuits have been programmed to remain in magnet-mode for as long as the magnetic field-detection sensor detects that one of the first, second and third static magnets is in close proximity to the AIMD.

3. The AIMD system of claim 1, wherein the magnetic field-detection sensor is configured to detect the close proximity of the first, second and third static magnets each having a strength of at least about 9 Gauss.

4. The AIMD system of claim 1, wherein the magnetic field-detection sensor is selected from the group of a reed switch, a Hall-effect sensor, and a giant magnetoresistive (GMR) sensor.

5. The AIMD system of claim 1, wherein the static strip magnet further comprises:
   a) a fourth static magnet connected to the third static magnet, wherein the fourth static magnet is of at least a fourth defined Gauss and of a north or south polarity that is the same polarity as that of the second static magnet; and
   b) a fifth static magnet connected to the fourth static magnet, wherein the fifth static magnet is of at least a fifth defined Gauss and of a north or south polarity that is the same polarity as that of the first and third static magnets.

6. The AIMD system of claim 5, wherein the magnetic field-detection sensor is configured to detect the close proximity of the first, second, third, fourth and fifth static magnets each having a strength of at least about 9 Gauss.

7. The AIMD system of claim 1, further comprising:
   a) an implanted lead wire connected to the AIMD, wherein the lead wire extends to a distal electrode configured to contact biological cells for providing electrical stimulation therapy to the biological cells and/or sensing electrical biological signals from body tissue, and
   b) wherein, upon commencement of magnet-mode, the electronic circuits have been programmed to cause electrical stimulation therapy of the body tissue and/or electrical sensing of biological signals from the body tissue through the lead wire to be suspended, maintained in a preset mode, and/or placed in a programmed mode.

8. The AIMD system of claim 7, wherein, upon commencement of magnet mode, the electronic circuits have been programmed to remain in magnet-mode for as long as the magnetic field-detection sensor detects that the static strip magnet is in close proximity to the AIMD.

9. An active implantable medical device (AIMD) system, comprising:
   a) an AIMD that is configured to deliver electrical stimulation therapy to body tissue and/or sense electrical biological signals from body tissue, wherein the AIMD comprises a housing containing a magnetic field-detection sensor connected to electronic circuits;
   b) a static strip magnet comprising:
      i) a first static magnet of at least a first defined Gauss and of a north polarity;
      ii) a second static magnet connected to the first static magnet, wherein the second static magnet is of at least a second defined Gauss and of a south polarity; and
      iii) a third static magnet connected to the second static magnet, wherein the third static magnet is of at least a third defined Gauss and of a north polarity,
   c) wherein the electronic circuits of the AIMD have been programmed to register when the static strip magnet has been swiped across the AIMD so that when the magnetic field-detection sensor detects a defined north and south polarity sequence of the first, second and third magnets, the electronic circuits have been programmed to enter into magnet-mode with electrical stimulation therapy of the body tissue and/or electrical sensing of biological signals from the body tissue being suspended, maintained in a preset mode, and/or placed in a programmed mode.

10. The AIMD system of claim 9, wherein, upon commencement of magnet-mode, the electronic circuits have been programmed to remain in magnet-mode for as long as the magnetic field-detection sensor detects that one of the first, second and third static magnets is in close proximity to the AIMD.

11. The AIMD system of claim 9, wherein the magnetic field-detection sensor is configured to detect the close proximity of the first, second and third static magnets each having a strength of at least about 9 Gauss.

12. The AIMD system of claim 9, wherein the magnetic field-detection sensor is selected from the group of a reed switch, a Hall-effect sensor, and a giant magnetoresistive (GMR) sensor.

13. The AIMD system of claim 9, wherein the static strip magnet further comprises:

a) a fourth static magnet connected to the third static magnet, wherein the fourth static magnet is of at least a fourth defined Gauss and of a south polarity; and
b) a fifth static magnet connected to the fourth static magnet, wherein the fifth static magnet is of at least a fifth defined Gauss and of a north polarity.

14. The AIMD system of claim 13, wherein the magnetic field-detection sensor is configured to detect the close proximity of the first, second, third, fourth and fifth static magnets each having a strength of at least about 9 Gauss.

15. The AIMD system of claim 9, further comprising:
a) an implanted lead wire connected to the AIMD, wherein the lead wire extends to a distal electrode configured to contact biological cells for providing electrical stimulation therapy to the biological cells and/or sensing electrical biological signals from body tissue, and
b) wherein, upon commencement of magnet-mode, the electronic circuits have been programmed to cause electrical stimulation therapy of the body tissue and/or electrical sensing of biological signals from the body tissue through the lead wire to be suspended, maintained in a preset mode, and/or placed in a programmed mode.

16. The AIMD system of claim 15, wherein, upon commencement of magnet mode, the electronic circuits have been programmed to remain in magnet-mode for as long as the magnetic field-detection sensor detects that the static strip magnet is in close proximity to the AIMD.

17. A method for an active implantable medical device (AIMD) to enter into magnet-mode, the method comprising the steps of:
a) providing an AIMD that is implanted in body tissue and configured to deliver electrical stimulation therapy to body tissue and/or sense electrical biological signals from body tissue, wherein the AIMD has a housing containing a magnetic field-detection sensor connected to electronic circuits, and wherein the electronic circuits have been programmed to register when the magnetic field-detection sensor detects that a static magnet of at least a defined Gauss field strength is in close proximity to the AIMD as a close proximity occurrence and when the static magnet is not in close proximity to the AIMD as a removal occurrence;
b) providing a static strip magnet comprising:
i) a first static magnet of at least a first defined Gauss and of a north or south polarity;
ii) a second static magnet connected to the first static magnet, wherein the second static magnet is of at least a second defined Gauss and of a north or south polarity that is opposite the polarity of the first static magnet; and
iii) a third static magnet connected to the second static magnet, wherein the third static magnet is of at least a third defined Gauss and of a north or south polarity that is the same polarity as that of the first static magnet; and
c) moving the static magnet into close proximity to the AIMD so that when the electronic circuits register that the magnetic field-detection sensor detects a defined north and south polarity sequence of the first, second and third magnets, the electronic circuits have been programmed to enter into magnet-mode with electrical stimulation therapy of the body tissue and/or electrical sensing of biological signals from the body tissue being suspended, maintained in a preset mode, and/or placed in a programmed mode.

18. The method of claim 17, including, upon commencement of magnet-mode, the electronic circuits have been programmed to remain in magnet-mode for as long as the magnetic field-detection sensor detects that one of the first, second and third static magnets is in close proximity to the AIMD.

19. The method of claim 17, including providing the first, second and third static magnets each having a strength of at least about 9 Gauss.

20. The method of claim 17, including selecting the magnetic field-detection sensor from the group of a reed switch, a Hall-effect sensor, and a giant magnetoresistive (GMR) sensor.

* * * * *